(12) United States Patent
Notohardjono et al.

(10) Patent No.: US 11,890,224 B2
(45) Date of Patent: Feb. 6, 2024

(54) COOLING APPARATUSES WITH PHYSICALLY-POWERED, MECHANICAL COOLANT PUMPS

(71) Applicant: INTERNATIONAL BUSINESS MACHINES CORPORATION, Armonk, NY (US)

(72) Inventors: Budy Notohardjono, Poughkeepsie, NY (US); Yuanchen Hu, Wappingers Falls, NY (US); Robert K. Mullady, Ulster, NY (US); Milnes P. David, New Paltz, NY (US); Levi Campbell, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 289 days.

(21) Appl. No.: 17/474,272

(22) Filed: Sep. 14, 2021

(65) Prior Publication Data

US 2023/0077722 A1 Mar. 16, 2023

(51) Int. Cl.
*A61F 7/00* (2006.01)
*A61F 2/80* (2006.01)

(52) U.S. Cl.
CPC .............. *A61F 7/0085* (2013.01); *A61F 2/80* (2013.01); *A61F 2007/0029* (2013.01);
(Continued)

(58) Field of Classification Search
CPC .... A61F 2/70; A61F 2/748; A61F 2/80; A61F 2002/5003; A61F 2002/5032; A61F 2002/5033; A61F 2002/5035; A61F 2002/5073; A61F 2002/5075; A61F 2002/5079; A61F 2002/6881; A61F 2002/704; A61F 2002/705; A61F 2007/0029; A61F 2007/0039;
(Continued)

(56) References Cited

U.S. PATENT DOCUMENTS

| 6,423,098 B1 | 7/2002 | Beidermann |
| 6,443,993 B1 | 9/2002 | Koniuk |

(Continued)

FOREIGN PATENT DOCUMENTS

| CN | 111772890 A | 10/2020 |
| CN | 111772891 A | 10/2020 |
| CN | 213851270 U | 8/2021 |

OTHER PUBLICATIONS

International Search Report and Written Opinion for PCT/EP2022/073622, dated Nov. 25, 2022 (9 pages) (Year: 2022).

(Continued)

*Primary Examiner* — Tigist S Demie
(74) *Attorney, Agent, or Firm* — Tihon Poltavets, Esq.; Kevin P. Radigan, Esq.; HESLIN ROTHENBERG FARLEY & MESITI P.C.

(57) ABSTRACT

Apparatuses and methods of fabrication are provided which include a mechanical coolant pump to facilitate pumping a coolant through a coolant loop. The mechanical coolant pump is to couple to an individual and be physically powered by a specified movement of the individual to pump coolant. Coolant pumped by the mechanical coolant pump is circulated by the coolant pump through a device associated with the individual to cool the device.

20 Claims, 22 Drawing Sheets

(52) U.S. Cl.
CPC .......... *A61F 2007/0039* (2013.01); *A61F 2007/0051* (2013.01); *A61F 2007/0056* (2013.01)

(58) Field of Classification Search
CPC ...... A61F 2007/0051; A61F 2007/0056; A61F 7/0085; F28D 1/047; F28D 15/00; F28F 1/325
See application file for complete search history.

(56) References Cited

U.S. PATENT DOCUMENTS

| | | | |
|---|---|---|---|
| 7,500,985 | B2 | 3/2009 | Saadat |
| 8,652,218 | B2 | 2/2014 | Goldfarb et al. |
| 2005/0246826 | A1 | 11/2005 | McCarter et al. |
| 2007/0055383 | A1* | 3/2007 | King .......... A61F 2/70 623/34 |
| 2014/0046455 | A1 | 2/2014 | Herr et al. |
| 2014/0309750 | A1 | 10/2014 | Kelley et al. |
| 2016/0067062 | A1 | 3/2016 | Jorgensen et al. |
| 2019/0117420 | A1 | 4/2019 | Storup |

OTHER PUBLICATIONS

Mel et al., "The NIST Definition of Cloud Computing," National Institute of Standards and Technology, Information Technology Laboratory, Special Publication 800-145, Sep. 2011 (pp. 1-7).

IBM Publication, "z/Architecture Principles of Operation," IBM® Publication No. SA22-7832-12, 13th Edition, Sep. 2019 (pp. Jan. 2000).

Dowd, Garrett, "Prosthetic Thermal Management Device", (Year: 2015). Honors Research Projects. 196. http://ideaexchange.uakron.edu/honors_research_projects/196 (28 pages).

Pace, Eileen, "Vet's Self-Cooling Prosthetic Could Help Amputees Beat the Heat", NPR Radio, (Year: 2014) https://www.npr.org/2014/11/11/363313691/vest-self-cooling-prosthetic- . . . (5 pages).

IBM, "Liquid Cooling for Medical Devices", U.S. Appl. No. 16/911,452, filed Jun. 25, 2020 (25 pages).

* cited by examiner

COOLING APPARATUSES WITH PHYSICALLY-POWERED, MECHANICAL COOLANT PUMPS

BACKGROUND

A prosthesis is an artificial substitute or replacement for a part of an individual's body, such as a leg or arm. Prostheses are designed for functional or cosmetic reasons, or both. In one or more implementations, certain prostheses include a prosthetic socket, which is the device that joins, for instance, an individual's residual limb to a prosthetic limb. The prosthetic socket is tailored to the individual, based on the condition and shape of the residual limb. For a prosthesis to function well, the prosthetic socket needs to be a good fit to the individual.

Heat and perspiration of an individual within a prosthetic socket are often some of the biggest problems expressed by the users of prosthetic limbs.

SUMMARY

Certain shortcomings of the prior art are overcome and additional advantages are provided through the provision, in one or more aspects, of an apparatus, which includes a mechanical coolant pump. The mechanical coolant pump facilitates pumping a coolant through a coolant loop. The apparatus is to couple to an individual, and the mechanical coolant pump is physically powered by a specified movement of the individual to pump coolant. Coolant pumped by the mechanical coolant pump is circulated by the coolant loop through a device associated with the individual to cool the device.

In another embodiment, an apparatus is provided which includes a mechanical coolant pump to facilitate pumping a coolant through a coolant loop. The apparatus is to couple to an individual, and the mechanical coolant pump is physically powered by a specified movement of the individual to pump coolant. Coolant pumped by the mechanical coolant pump is circulated by the coolant loop through a prosthetic socket of a prosthesis worn by the individual to coolant the prosthetic socket. In one embodiment, the mechanical coolant pump is coupled to the prosthesis.

In a further aspect, a method is provided which includes providing a mechanical coolant pump to facilitate pumping a coolant through a coolant loop. The mechanical coolant pump is physically powered to pump coolant with a specified movement of an individual, and the mechanical coolant pump is provided as part of a prosthesis to be worn by the individual. In operation, coolant pumped by the mechanical coolant pump is circulated by the coolant loop through a prosthetic socket of the prosthesis when worn by the individual to coolant the prosthetic socket.

Additional features and advantages are realized through the techniques described herein. Other embodiments and aspects of the invention are described in detail herein and are considered a part of the claimed aspects.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Figure 1:
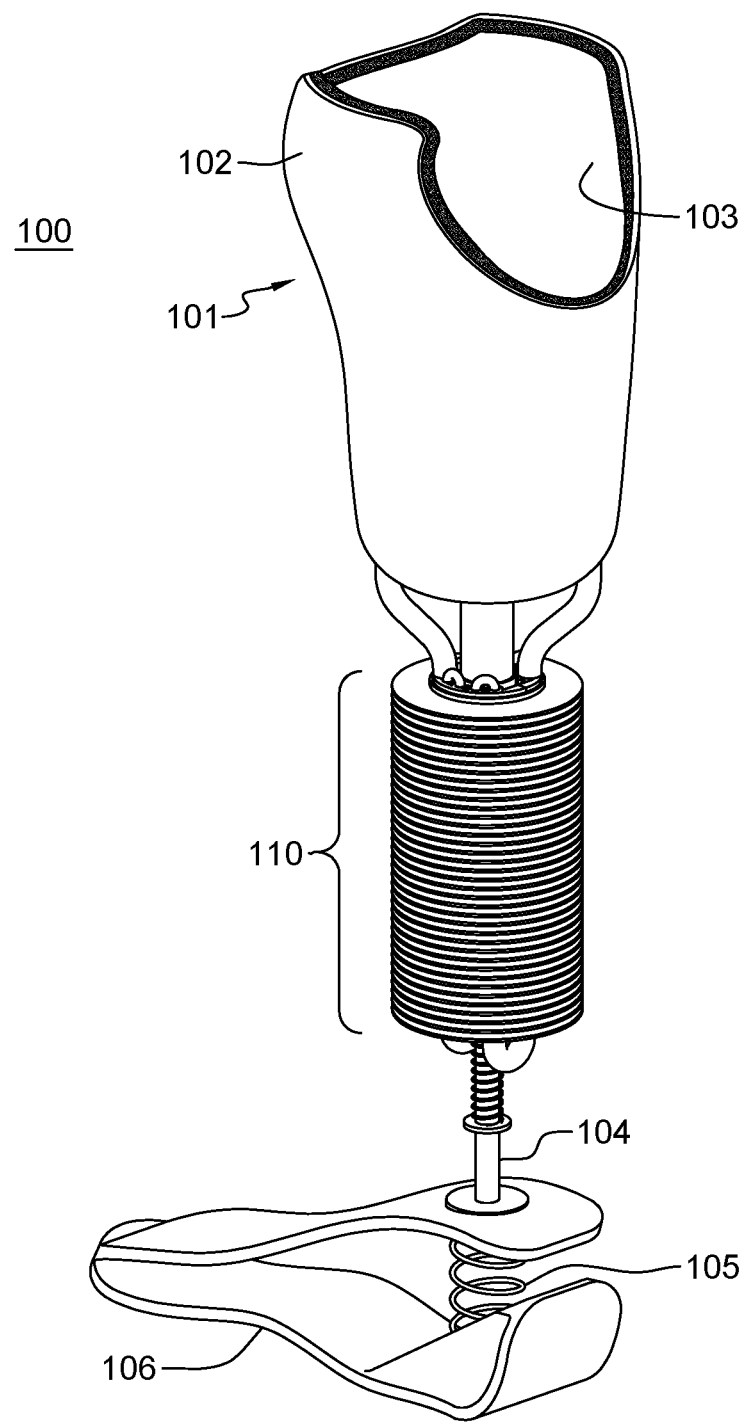
FIG. 1 depicts one embodiment of an apparatus for cooling a prosthesis, and which includes a coolant loop and a cooling device with a mechanical coolant pump, in accordance with one or more aspects of the present invention.

Aspects of the present invention and certain features, advantages, and details thereof, are explained more fully below with reference to the non-limiting example(s) illustrated in the accompanying drawings. Descriptions of well-known materials, fabrication tools, processing techniques, etc., are omitted so as not to unnecessarily obscure the invention in detail. It should be understood, however, that the detailed description and the specific example(s), while indicating aspects of the invention, are given by way of illustration only, and are not by way of limitation. Various substitutions, modifications, additions, and/or arrangements, within the spirit and/or scope of the underlying inventive concepts will be apparent to those skilled in the art for this disclosure. Note further that reference is made below to the drawings, which are not drawn to scale for ease of understanding, wherein the same reference numbers used throughout different figures designate the same or similar components. Also, note that numerous inventive aspects and features are disclosed herein, and unless otherwise inconsistent, each disclosed aspect or feature is combinable with any other disclosed aspect or feature as desired for a particular application.

Disclosed herein are apparatuses and methods which facilitate cooling a device associated with an individual, such as a device worn by the individual. By way of example, in one or more embodiments, the device to be cooled can be part of a medical device worn by the individual, such as a prosthesis. In one particular embodiment, the device to be cooled is a prosthetic socket of a prosthetic limb worn by the individual.

The apparatuses disclosed include a cooling device which includes a mechanical coolant pump driven by a specified movement of the individual with whom the device to be cooled is associated. The specified movement physically powers the mechanical coolant pump of the apparatus without any electrical power. In one or more embodiments, the movement of the individual physically powers the mechanical coolant pump to pump liquid coolant through a coolant loop passing through or associated with the device. For instance, in one or more or more embodiments, the apparatus is configured to facilitate cooling the individual's skin at the interface of the individual's body and device. For example, the apparatus is configured to facilitate lowering or maintaining temperature of skin within, for instance, a prosthetic socket, to a comfortable level, such as during heightened levels of physical activity. By lowering skin temperature, the apparatus is able to advantageously reduce or inhibit perspiration on the skin of the individual at the interface with the device.

Note that although primarily discussed herein as being applied to a prosthesis, the apparatuses and methods described are not limited to use with prosthetic devices, and it will be appreciated by those of ordinary skill in the art that the apparatuses and methods described can be adapted for use with a variety of devices that are placed, for instance, on, or in close contact with, the skin of an individual, to regulate the temperature of the device-to-skin interface. For instance, the apparatuses and methods described herein can be used to regulate skin temperature at the interface of an individual wearing an exoskeleton device, or wearing another device, where the device overlays the individual's skin, at least in part, such that comfort can be enhanced by a liquid coolant flow through a coolant loop passing through the device at, or adjacent to, the interface between the device and individual.

By way of example, FIG. 1 depicts one embodiment of an apparatus such as disclosed herein integrated into and forming part of an enhanced prosthesis 100. As described herein, the apparatus includes a cooling device 110 which includes a coolant loop, a mechanical coolant pump and a heat exchanger, in accordance with one or more aspects of the present invention. Prosthesis 100 of FIG. 1 illustrates one embodiment only of a prosthetic limb, and in particular, a prosthetic leg which can benefit from a cooling device such as described herein.

As illustrated, prosthesis 100 includes a prosthetic socket 101 which has, in one embodiment, a conforming socket body 102 (such as a conforming socket formed of a hard material), with one or more soft inner liners 103 for comfort at the interface between the individual and prosthetic socket. In operation, prosthetic socket 101 is configured or tailored to receive a respective body part of the individual to wear prosthesis 100. In the illustrated prosthetic leg example, prosthesis 100 includes, along with the cooling device, a support structure 104 (such as a metal rod), a spring 105 and prosthetic foot 106, designed, by way of example, to facilitate movement of the individual wearing the prosthesis. Note that there are a wide variety of prostheses available which include a prosthetic socket, such as prosthetic socket 101, and that receives a respective body part of the individual for which it is configured. As noted, excessive heat and perspiration of the individual at the interface where the prosthetic device attaches to the individual are common complaints expressed by people when wearing prosthetic devices.

Figure 2:
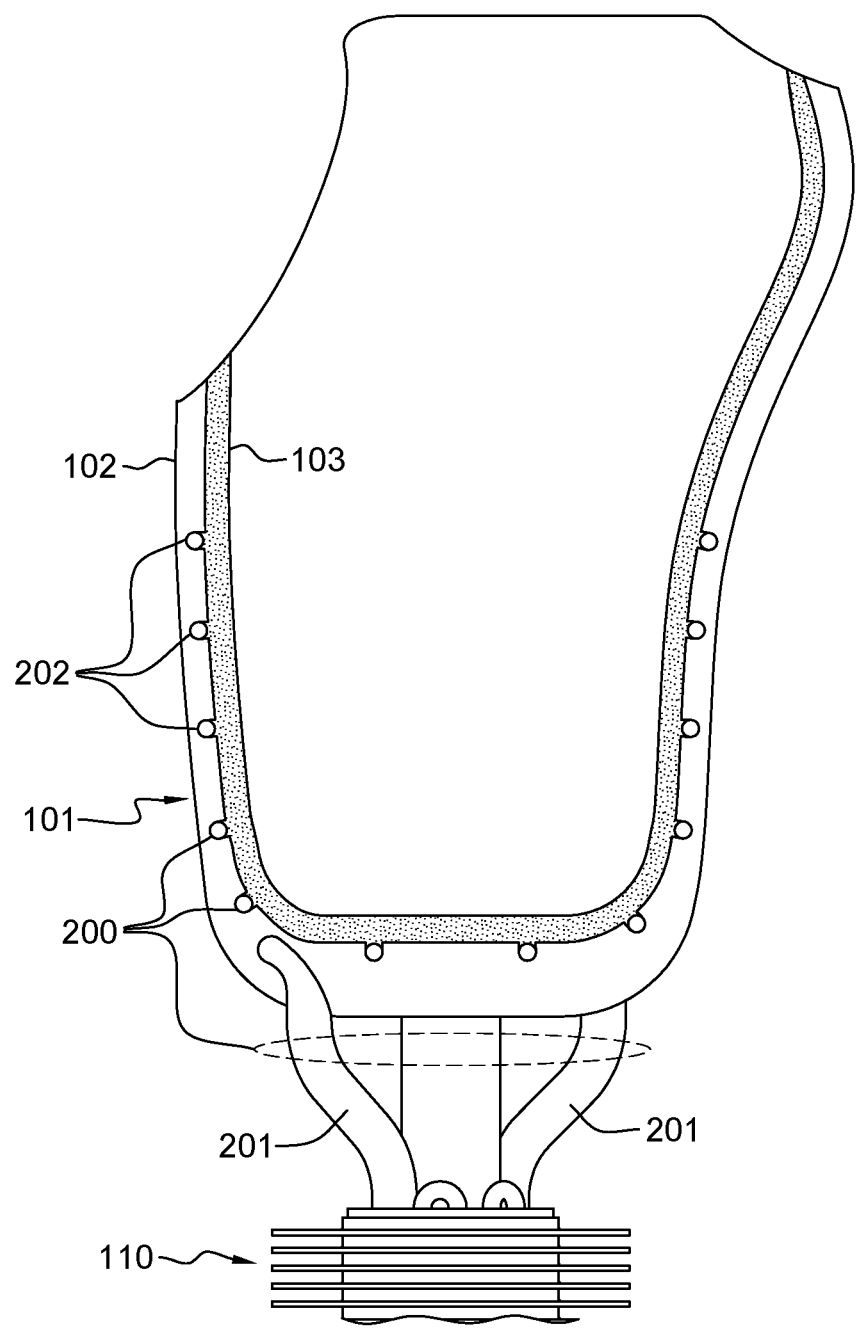
FIG. 2 is a partial breakaway view of the apparatus of FIG. 1, in accordance with one or more aspects of the present invention.

FIG. 2 depicts a partial cross-sectional view of prosthesis 100 of FIG. 1, depicting a coolant loop 200 passing through, in one embodiment, the inside of prosthetic socket 101, for instance, at the inner surface of socket body 102, to facilitate passing liquid coolant at or near the interface of the individual's body with the socket. In one or more implementations, tubing 202 of coolant loop 200 can be placed into, for instance, one or more grooves, in the inner surface of the prosthetic device in contact with one or more soft liners 103. For instance, tubing can be molded into the inner surface of socket body 102 in a manner so as to not affect the mechanical strength of the socket body. If desired, in one embodiment, one or more temperature sensors (not shown) can also be provided at, for instance, the inner surface of socket body 102 and the liner(s) 103 to measure a temperature related to the individual's skin temperature within the socket and provide feedback to, for instance, an electronic controller controlling one or more adjustable coolant flow valves associated with the mechanical coolant pump of the cooling device, such as described below with reference to the embodiment of FIG. 4C. In one or more embodiments, coolant loop 200 is configured to include one or more fluid-flow channels through the prosthetic socket as desired to facilitate cooling the skin of the individual wearing the device near or at the individual-to-device interface. In one or more embodiments, these fluid channels are disposed on the inner surface of the prosthetic device in direct contact with the liner and/or the individual. By way of example, the fluid channels can be made of relatively thick tubing 202, such as thick copper tubing embedded within the inner surface of the socket body, and can be configured to receive fluid from the cooling device 110 via tubing or hoses 201 connecting the socket tubing 202 or fluid channel(s) to the cooling device.

In exemplary embodiments, cooling devices 110 such as discussed herein are configured to pump liquid coolant, as well as reduce the temperature of the liquid coolant. In one embodiment, the liquid coolant can be water or an aqueous-based coolant. However, the concepts disclosed herein are readily adapted to use with other types of coolant, while still maintaining the advantages and unique features of the present invention.

In one or more embodiments, the cooling device includes, for instance, a mechanical coolant pump and a coolant-to-air heat exchanger, with the mechanical coolant pump being configured to circulate liquid coolant within the coolant loop between the cooling device and the device to be cooled. By way of example, FIGS. 3A & 3B depict exemplary embodiments of a cooled apparatus which includes a cooling device, in accordance with one or more aspects of the present invention.

Figure 3B:
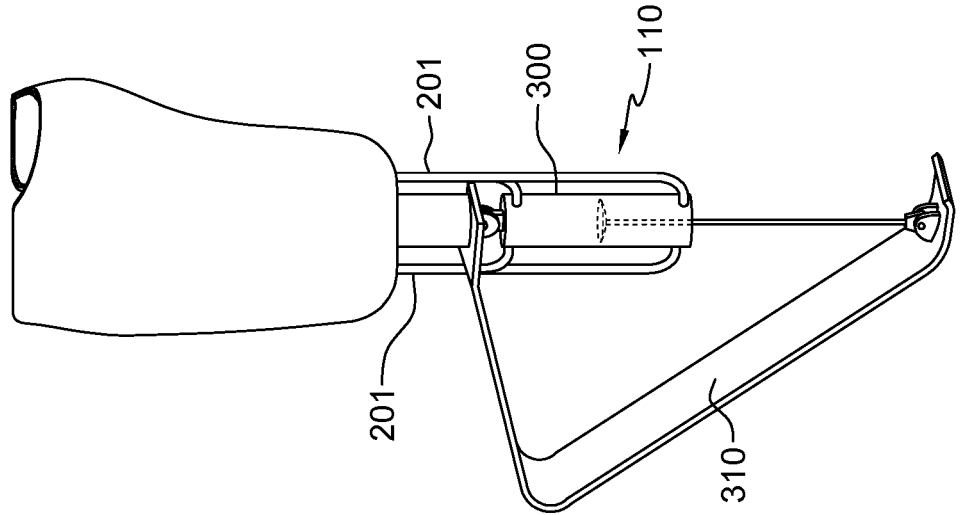
FIG. 3B depicts an alternate embodiment of an apparatus, in accordance with one or more aspects of the present invention.
Figure 3A:
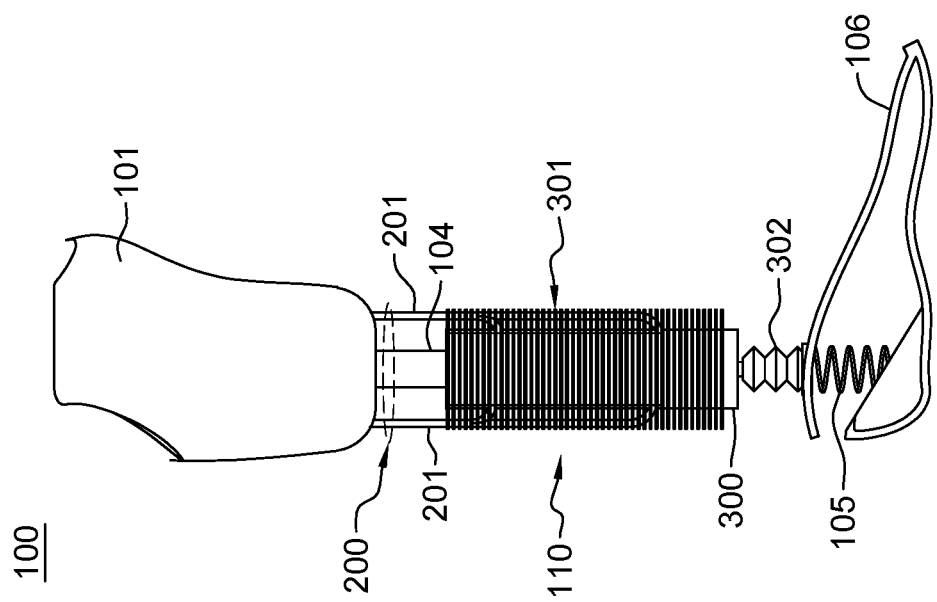
FIG. 3A is an elevational view of the apparatus of FIGS. 1 & 2, in accordance with one or more aspects of the present invention.

FIG. 3A depicts prosthetic leg 100 of FIGS. 1-2, which as noted includes a prosthetic socket 101, such as described above in connection with FIGS. 1 & 2, as well as a support column 104 and a prosthetic foot 106. In the embodiment illustrated, a coolant loop 200 includes coolant supply and return hoses 201, which facilitate the flow of liquid coolant between, for instance, tubing (or channels) within prosthetic socket 101 and a cooling device 110.

As illustrated in FIG. 3A, in one or more embodiments, cooling device 110 is integrated into prosthetic leg 100, for instance, as part of the support column 104 of the prosthesis. In one or more implementations, cooling device 110 includes a mechanical coolant pump 300 and a heat sink 301. In the illustrated embodiment, heat sink 301 includes a plurality of thermally conductive fins extending from, for instance, a thermally conductive support structure (such as a cylindrical support) across or through which liquid coolant passes in one or more tubing sections, or channels, with the coolant being pumped by mechanical coolant pump 300. As illustrated in FIG. 3A, prosthetic leg 100 can include a spring 105 disposed, for instance, at the lower region of support column 104 to facilitate, at least in part, a walking or running movement of the individual wearing the prosthesis. As described herein, in one or more embodiments, a pump piston of mechanical coolant pump 300 can be coupled to a further spring 302 to facilitate pumping of coolant with one or more specified movements of the individual, such as a stepping motion during walking and running.

FIG. 3B depicts an alternate embodiment of a prosthesis 100', similar to prosthesis 100 of FIG. 3A, however, employing a spring-type support 310, such as a blade-type support. In the embodiment of FIG. 3B, cooling device 110 can be similarly constructed to that described with reference to FIG. 3A. However, in FIG. 3B, the heat exchanger is removed to facilitate illustrating tying of the pump piston of mechanical coolant pump 300 to the spring-type support 310 (in one embodiment). Further, FIG. 3B illustrates the pump piston dividing the pump housing into first and second coolant chambers, each with respective coolant return and coolant supply lines, as illustrated by the tubing of FIG. 3B, and described further below with reference to FIGS. 4A-4B.

Figure 4B:
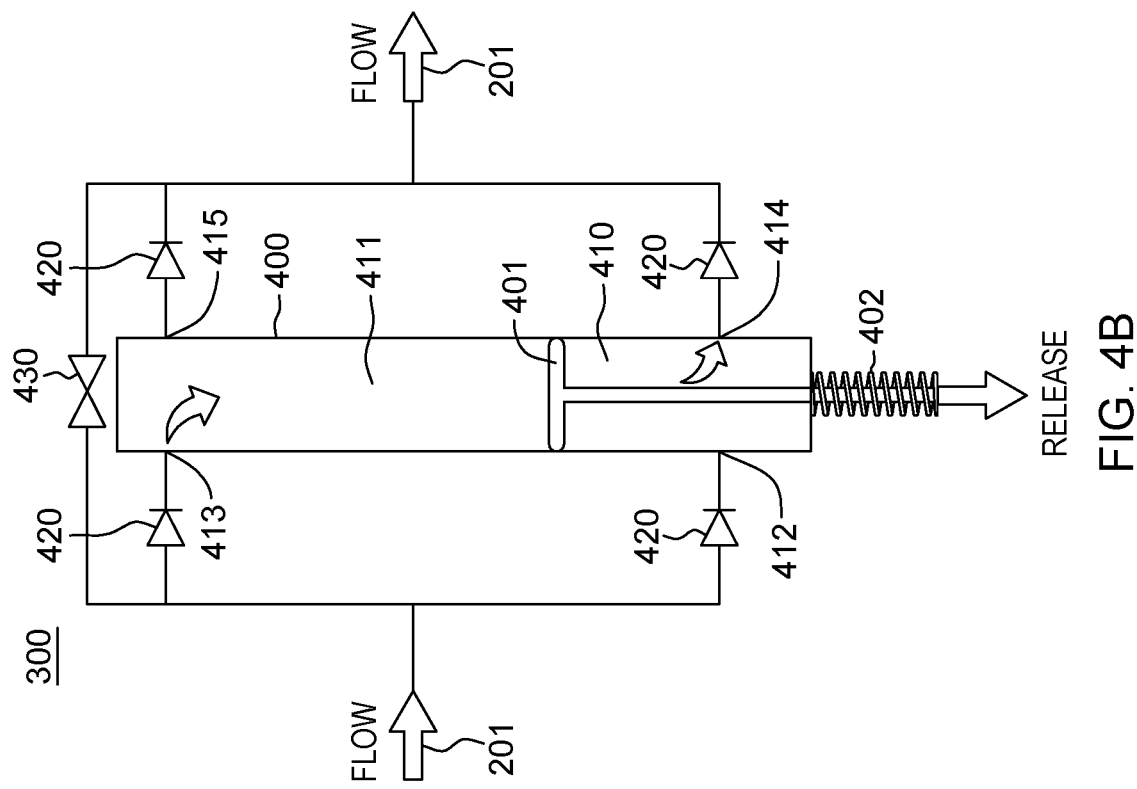
FIGS. 4A-4B depict an operational schematic of one embodiment of a mechanical coolant pump of an apparatus, in accordance with one or more aspects of the present invention.
Figure 4A:
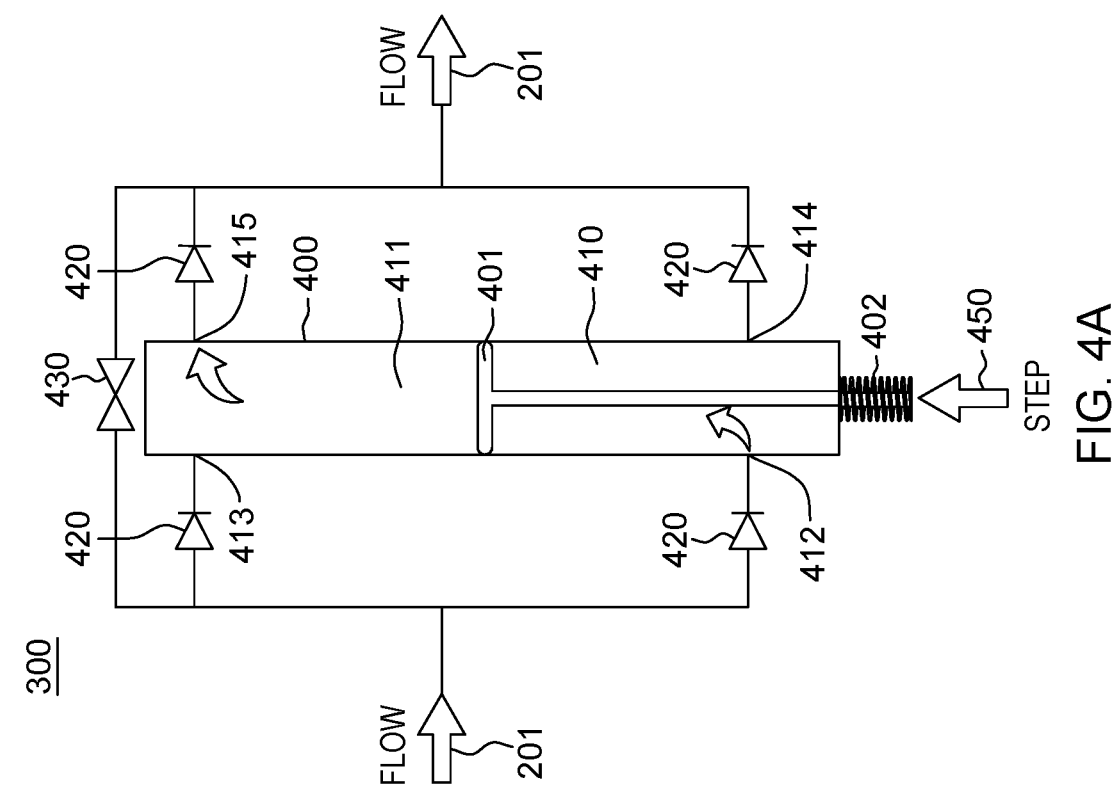

FIGS. 4A & 4B illustrate operational schematics of a mechanical coolant pump 300, in accordance with one or more aspects of the present invention. As noted, cooling apparatuses and methods are provided herein which include a mechanical coolant pump to facilitate pumping a coolant through a coolant loop, where the cooling apparatus, including the mechanical coolant pump, couples to (e.g., is worn by) an individual. The pump is physically powered by movement of the individual to pump coolant, such as with a stepping action during walking or running. Coolant pumped by the mechanical coolant pump circulates through the coolant loop passing through the device to be cooled, such as a prosthetic socket. Advantageously, the mechanical coolant pump is self-powered with, for instance, a minimal specified movement of the individual inducing a pumping action, which moves the liquid coolant and facilitates reducing temperature at the interface between the individual and device. In one or more implementations, the mechanical coolant pump is integrated within a prosthetic structure itself, and no external power source or battery is required to generate the pumping action since the pump operates mechanically, with the pumping action following naturally with the specified movement of the individual wearing the cooling apparatus.

Referring to FIGS. 4A & 4B, in one embodiment, mechanical coolant pump 300 includes a pump housing 400 and a pump piston 401, which reciprocates within pump housing 400 with movement of the individual and divides an inner sealed chamber of pump housing 400 into a first coolant chamber 410 and a second coolant chamber 411. In the embodiment depicted, the pump housing includes, or is coupled to, coolant return and supply lines 201, with the coolant return line feeding coolant to a first coolant inlet 412 of first coolant chamber 410, and to a second coolant inlet 413 of second coolant chamber 411, and with the coolant supply line receiving coolant from the respective coolant chambers via a first coolant outlet 414 and a second coolant outlet 415 of the pump housing 440, depending on the action of pump piston 401. In one embodiment, one or more check valves 420 are provided in line with the first and second coolant inlets 412, 413 and/or first and second coolant outlets 414, 415 to, for instance, prevent coolant backflow and ensure flow of coolant through the pump in the proper direction between the return and supply lines 201 of the coolant loop. Further, as illustrated, a bypass valve 430 can be provided to allow a controlled portion of coolant within the coolant loop to pass between the return and supply lines 201, without passing through pump housing 400 of mechanical coolant pump 300. Bypass valve 430 provides, in one embodiment, the individual with the ability to control the extent of coolant pumping pressure occurring within the apparatus with the individual's specified movement.

By way of example, where the device is a prosthesis, such as a prosthetic leg, and the cooling device, including the mechanical coolant pump, is integrated into the prosthesis, such as described herein, then with a stepping motion 450 of the individual on the prosthetic leg, the motion compresses a spring 402 (such as spring 302 or 310 in FIGS. 3A-3B), while also moving pump piston 401 upwards (in this example) to draw coolant into first chamber 410 through first coolant inlet 412, concurrently pushing coolant from second chamber 411 through second coolant outlet 415. Release from the specified movement, as illustrated in FIG. 4B, allows spring 402 to move pump piston 401 in the opposite, downward direction (in one embodiment) within pump housing 400, drawing coolant into second coolant chamber 411 through second coolant inlet 413, concurrently pushing coolant from first coolant chamber 410 through first coolant outlet 414. In this manner, the individual's movement physically powers the mechanical coolant pump to drive or pump coolant through the coolant loop, and thereby facilitate cooling of the device-to-individual interface, such as a prosthetic socket-to-limb interface. Note that this discussion also assumes that, in one or more embodiments, a heat exchanger 301 (FIG. 3A) is associated with the cooling device, such as in an outer structure around the coolant pump, to facilitate extracting heat from coolant as the coolant passes through the cooling device.

Figure 4C:
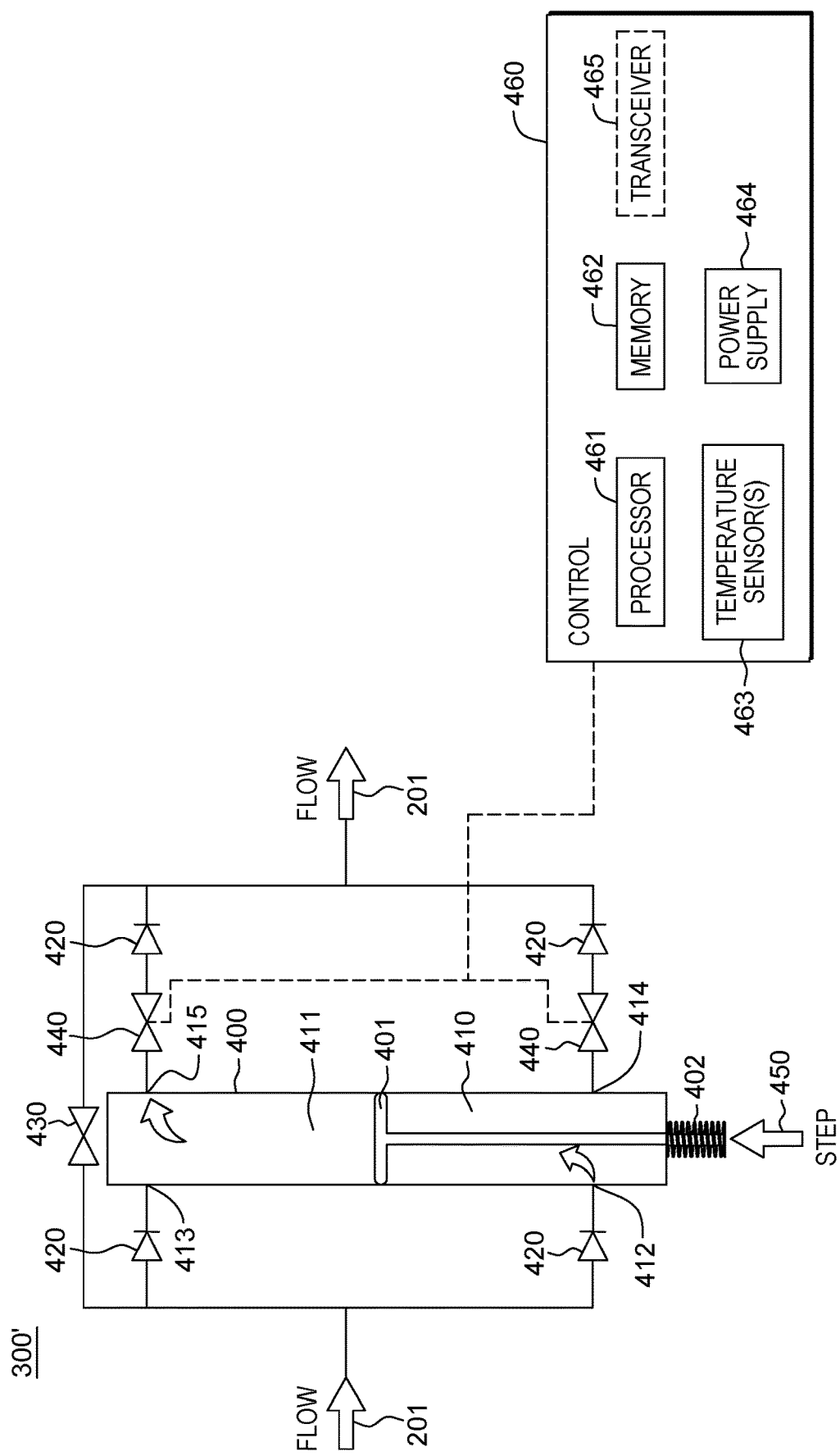
FIG. 4C is a schematic of another embodiment of a mechanical coolant pump of an apparatus, in accordance with one or more aspects of the present invention.

FIG. 4C is a schematic of another embodiment of a mechanical coolant pump 300', similar to mechanical coolant pump 300 described above in connection with FIGS. 3A-4B. In the embodiment of FIG. 4C, however, one or more adjustable valves 440 are provided, for instance, at the first and second coolant outlets from the pump housing. Adjustable valves 440 can be mechanically or electronically controlled based, for instance, on the individual's weight and activity levels, to control dampening of the apparatus with the individual's movement. Adjustable valves 440 will not significantly affect cooling of the apparatus but can add a comfort level by controlling the rate of compression/expansion, or the dampening action, of the mechanical coolant pump as the pump piston is raised and lowered with the specified individual movement and the biasing of the spring.

By way of example, in one or more embodiments, adjustable valves 440 can be adjustable electronic valves, and a control 460 or controller can be provided in association with the apparatus, for instance, integrated with the prosthetic limb. In one embodiment, control 460 can include a processor 461 or microcontroller, memory 462, one or more temperature sensors 463, a power supply 464, and optionally, a transceiver 465. In one embodiment, processor 461 and memory 462 are programmed or configured with code to control the adjustable valves 440, depending on the user's activity and comfort settings. In one embodiment, processor 461 can include a field-programmable gate array (FPGA), an application-specific integrated circuit (ASIC), and/or a general purpose processor configured to control operation of adjustable valve(s) 440 based, for instance, on sensed temperature. Power supply 464 can provide power to the processor and include one or more energy storage devices, such as a battery, that provides operational power to the control for controlling the adjustable valve(s) 440. Temperature sensors 463 can be configured to monitor one or more of: the temperature of the air surrounding the cooling device, a temperature of coolant being supplied to the device being cooled, and/or temperature of coolant being returned from the device being cooled. In one or more implementations, transceiver 465, when provided, can be configured to facilitate communication between control 460 controlling the adjustable valve(s) 440 and one or more temperature sensors 463. In another embodiment, transceiver 465 can be configured to facilitate communication between control 460 and a separate computing device (not shown), such as a smartphone, tablet, or personal computer of the individual user.

By way of further example, FIGS. 5A-5I depict additional details of cooling device 110 described above in connection with FIGS. 3A, 4A & 4B. Referring collectively to FIGS. 5A-5I, cooling device 110 is, in one embodiment, integrated within a prosthesis 100 forming, for instance, a portion of the support structure in the example of a prosthetic leg. Coolant return and supply hoses 201 connect cooling device 110 and the portion of the coolant loop within the device to be cooled, such as at the prosthetic socket-to-individual limb interface in the prosthetic socket 101 example described. Cooling device 110 includes mechanical coolant pump 300 (such as described herein, including a pump piston 401 and spring 302), and a heat sink 301. In one embodiment, heat sink 301 includes a thermally conductive structure 501 with one or more channels or tubes sections 502 in contact with, for instance, the inner surface of thermally conductive structure 501, such that heat passes from coolant within the channels or tube sections 502 through the thermally conductive structure 501, to a plurality of thermally conductive fins 503, for dissipation to ambient air about cooling device 110.

In the embodiment of FIGS. 5A-5I, the plurality of thermally conductive fins 503 are illustrated in a horizontal orientation by way of example only. In one or more implementations, the thermally conductive structure 501, coolant tube sections 502, and plurality of thermally conductive fins 503 can be formed of the same or different thermally conductive material(s), such as the same metal material(s) or different metal materials. As coolant flows through the channels or tube sections 502, the liquid coolant cools by conduction of heat across thermally conductive structure 501 to the thermally conductive fins 503. One or more tube or hose sections 505 can be provided to couple in fluid communication the channels or tube sections 503 within heat sink 301 to the appropriate coolant inlet(s) or coolant outlet(s) of the mechanical coolant pump 300.

Figure 5A:
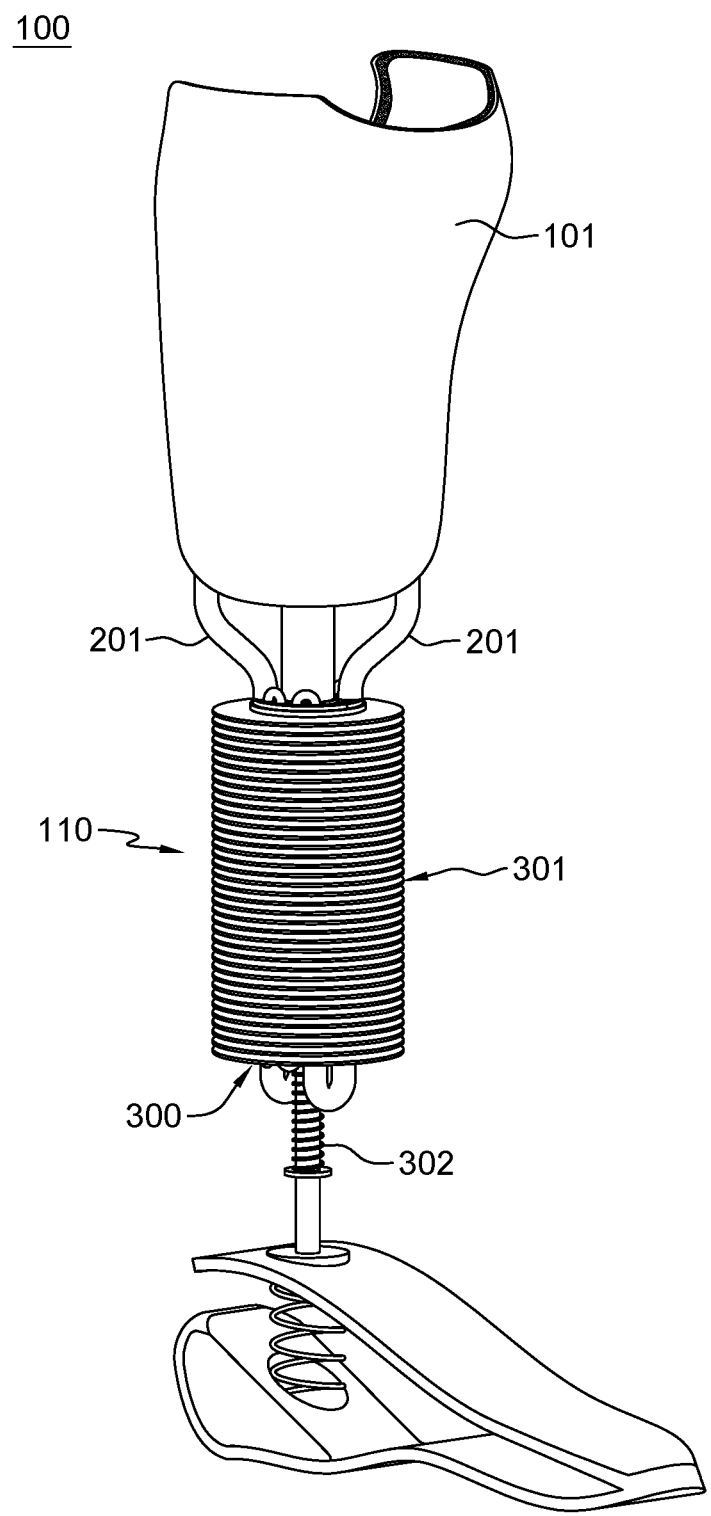
FIGS. 5A-5I depict various views of a more detailed embodiment of an apparatus, including a cooling device such as depicted in FIGS. 1-3A, in accordance with one or more aspects of the present invention.
Figure 5B:
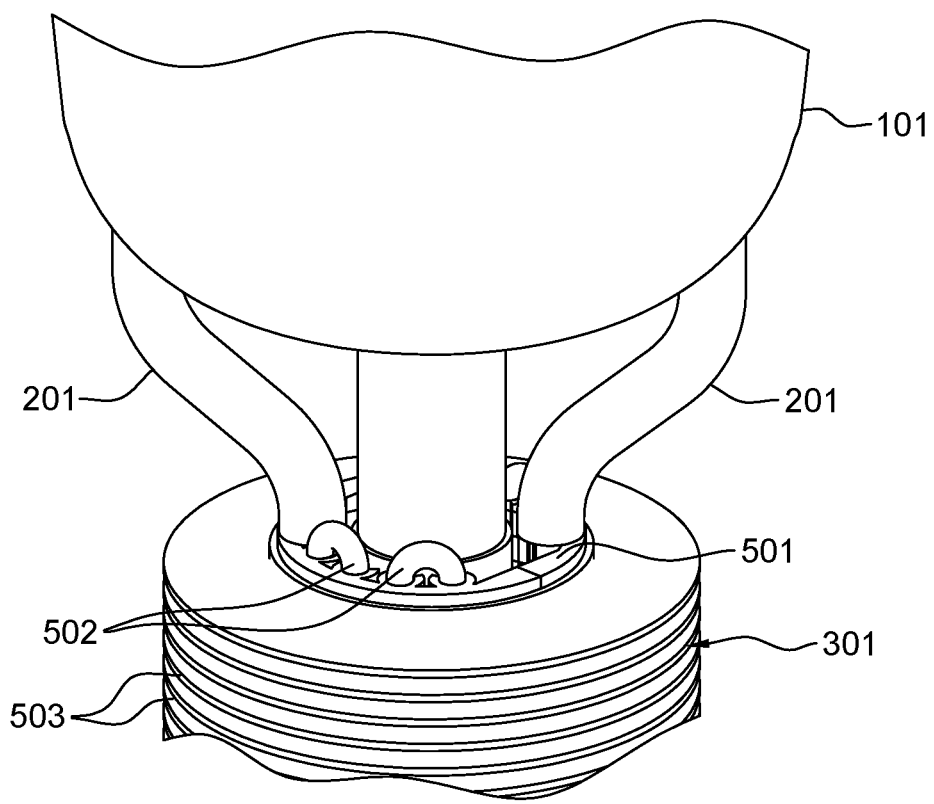
Figure 5C:
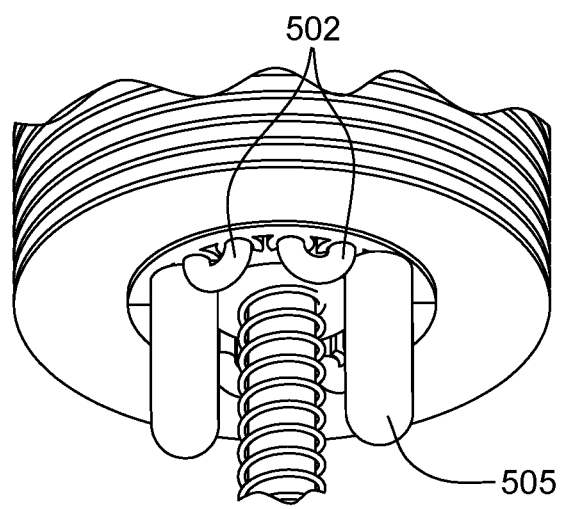
Figure 5D:
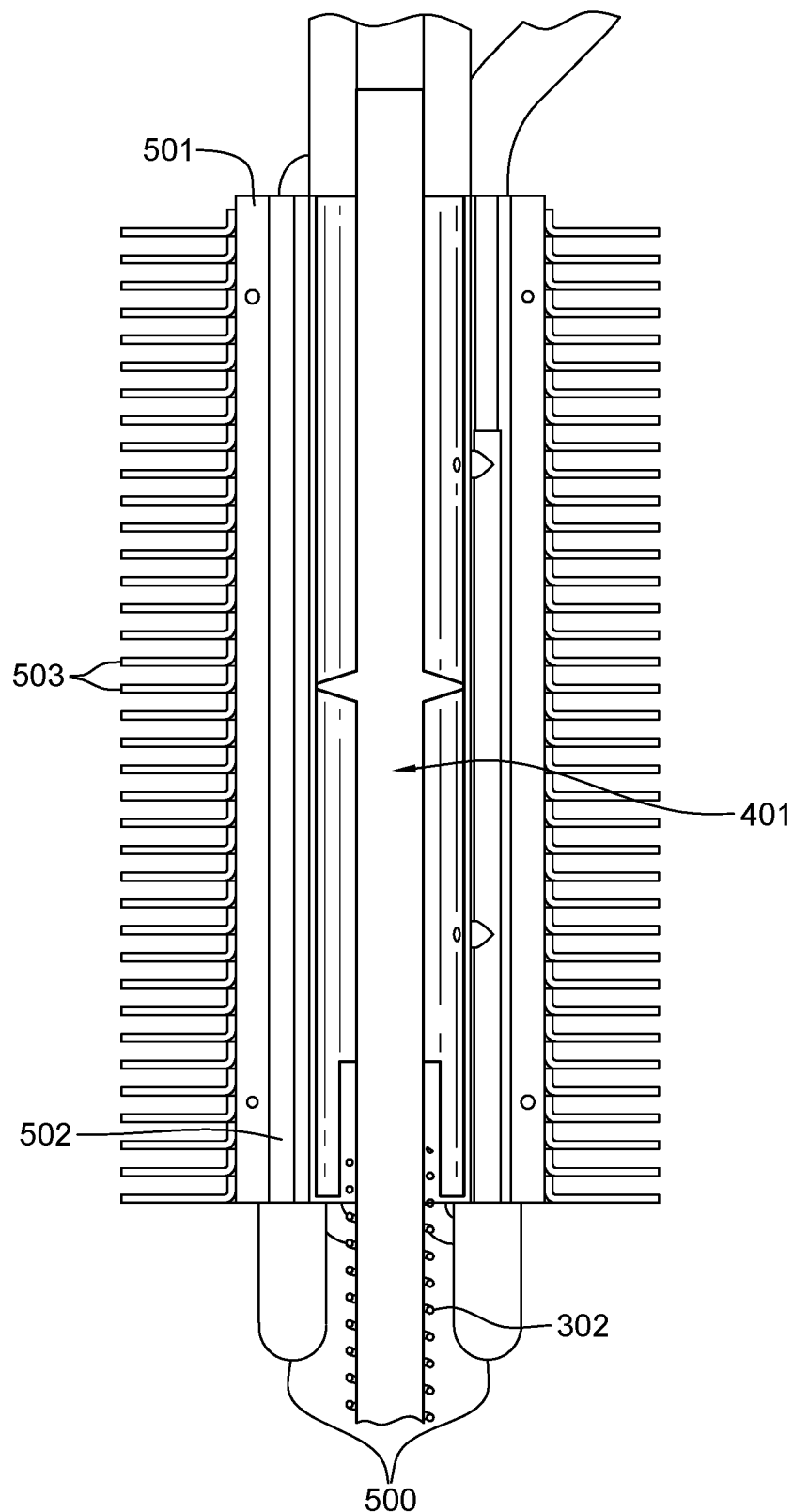
Figure 5E:
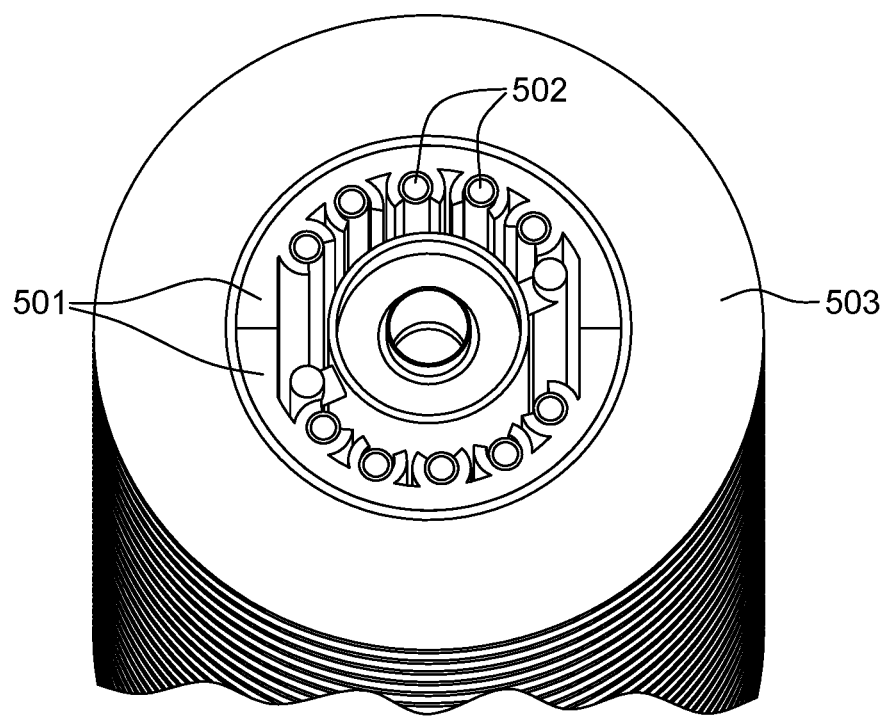
Figure 5F:
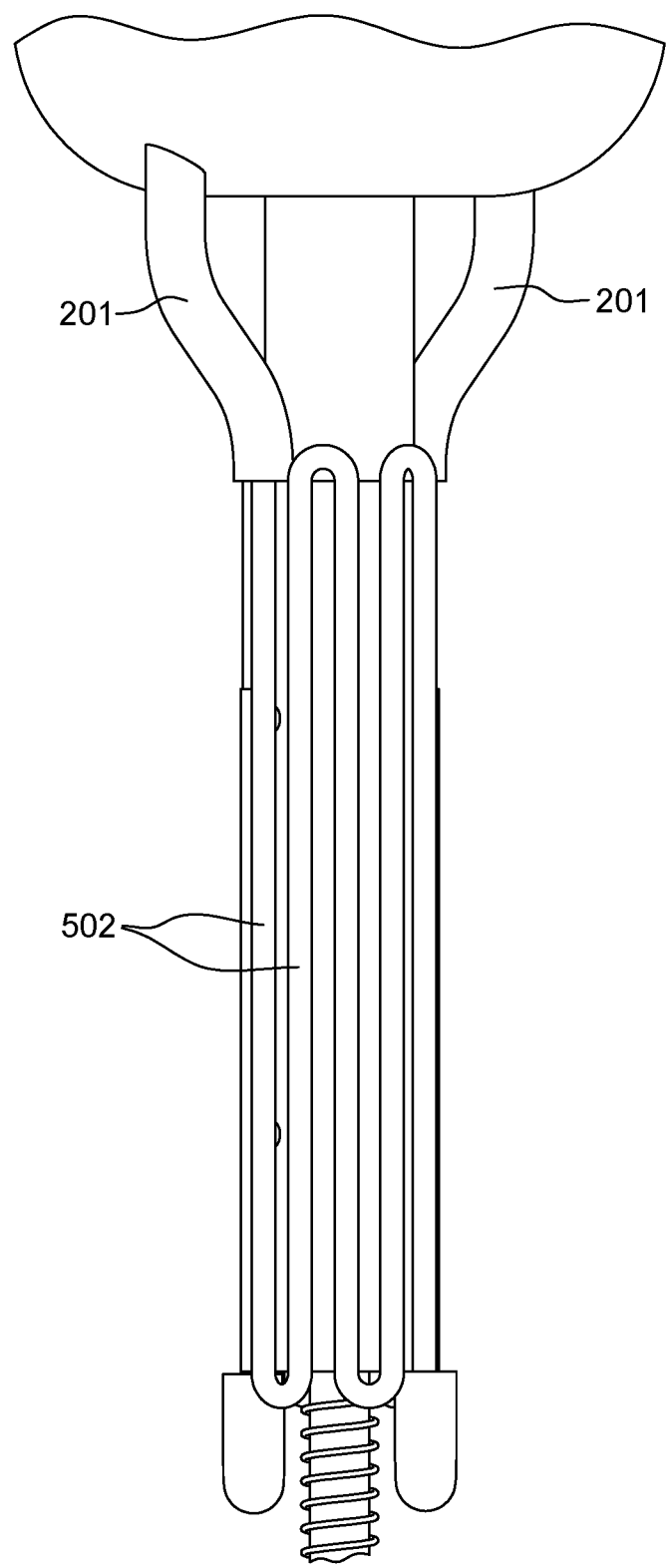
Figure 5G:
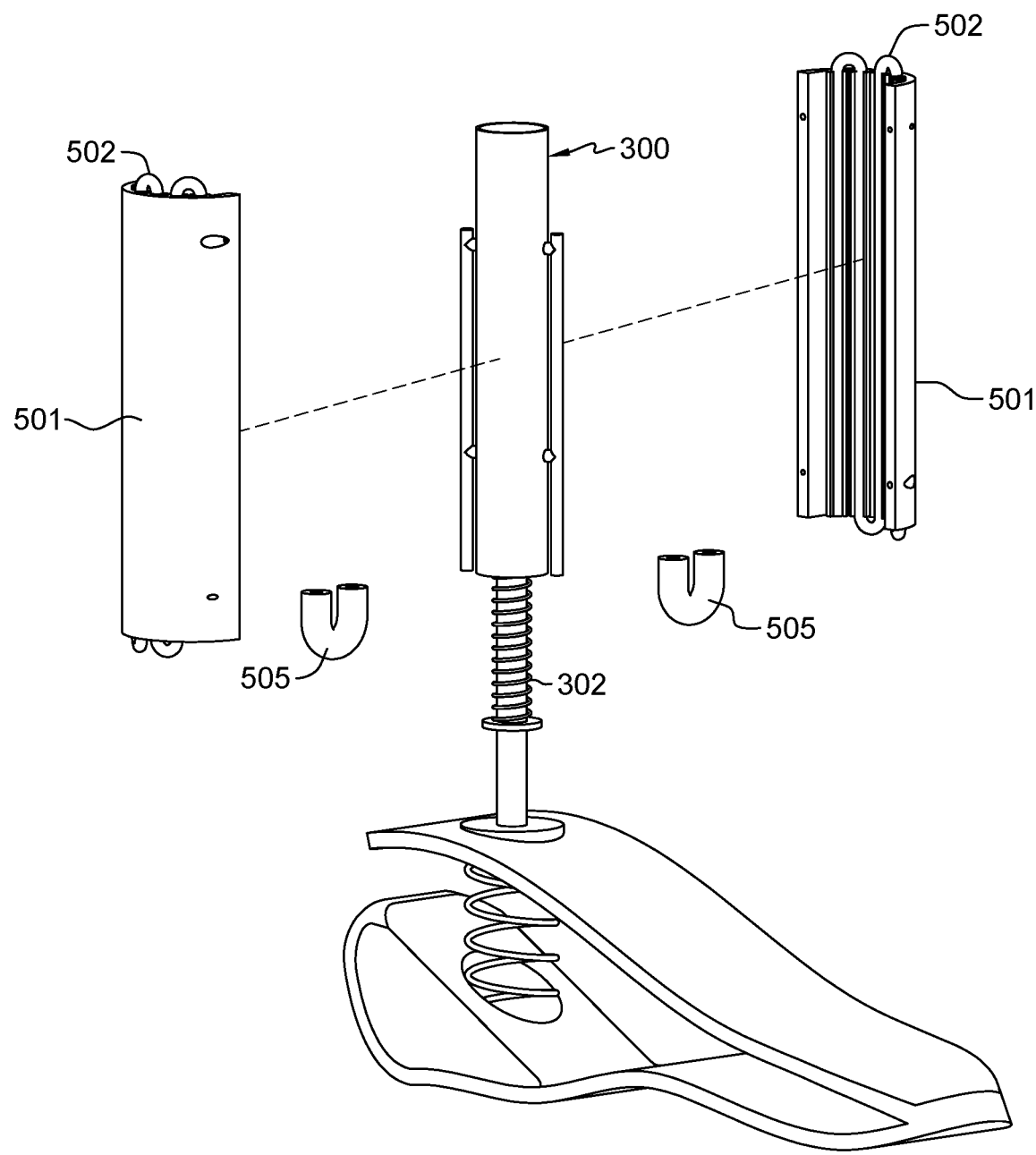
Figure 5H:
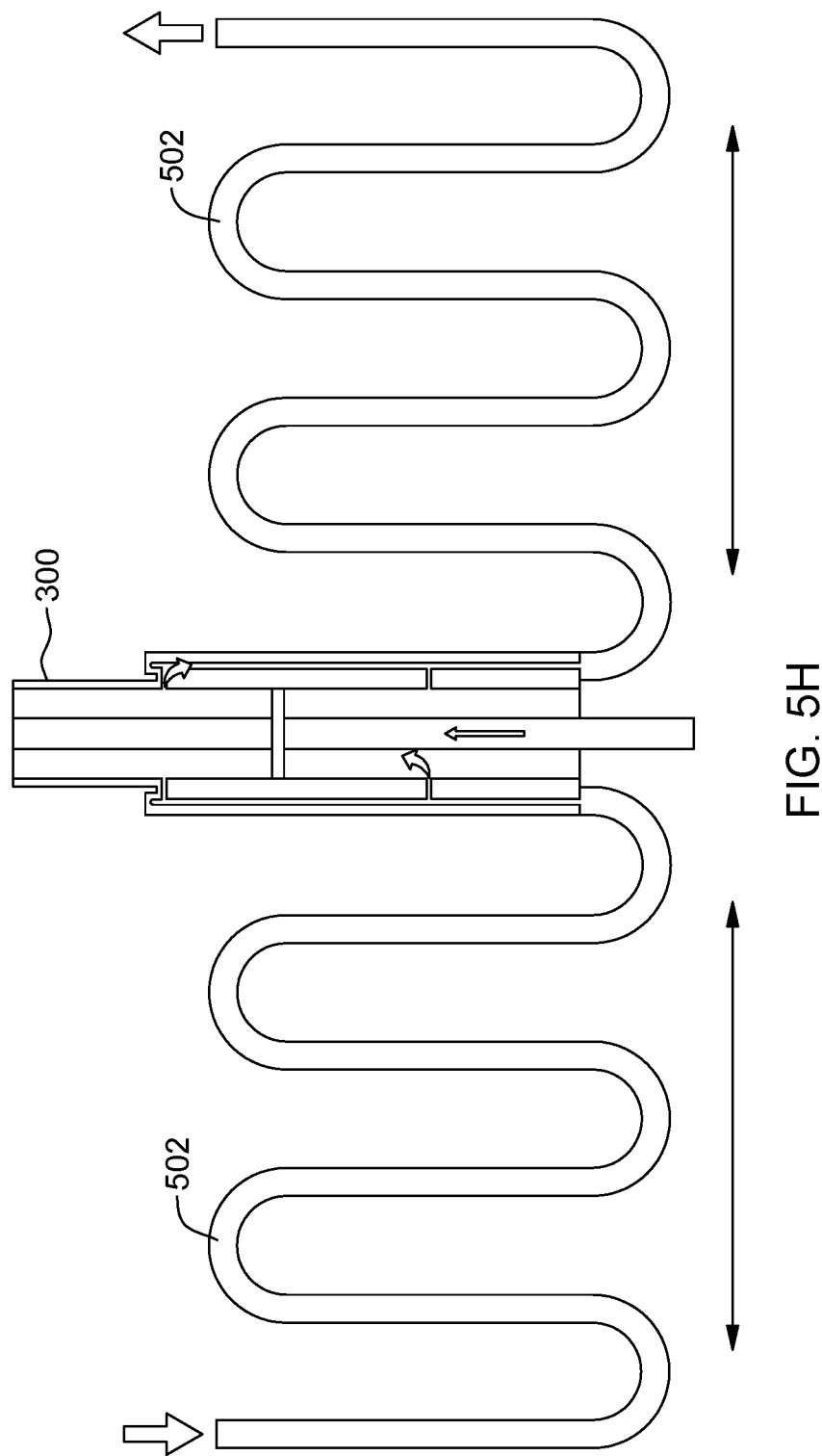
Figure 5I:
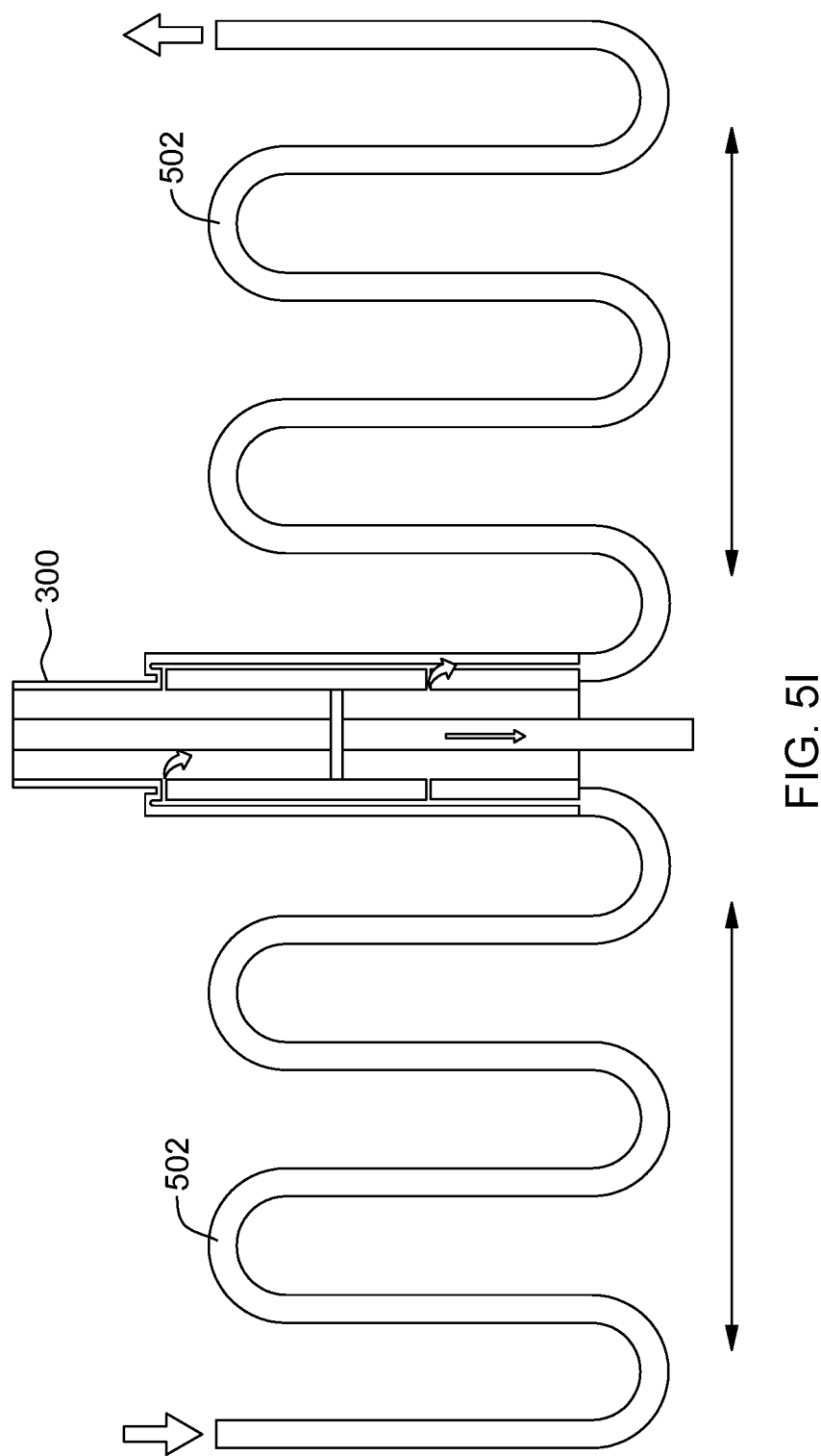

By way of example, FIGS. 5H & 5I illustrate one embodiment of flow of coolant through heat exchanger tubing, as well as the mechanical coolant pump. As illustrated, coolant flows through heat sink tube sections 502, transferring heat, via the thermally conductive structure 501, to the thermally conductive fins 503 for dissipation to the ambient air, with the coolant being pumped through the mechanical coolant pump as the individual moves by, for instance, stepping down on the prosthetic leg, and lifting up the prosthetic leg with, in one embodiment, the mechanical coolant pump spring being loaded to bias the pump piston in the downward direction, in one example. Those skilled in the art will note that other configurations of heat exchanger 300 can be used. For instance, in one or more other embodiments, the channels or tubing sections 502 within heat sink 301 can be in direct contact with the plurality of thermally conductive fins 503.

Figure 6:
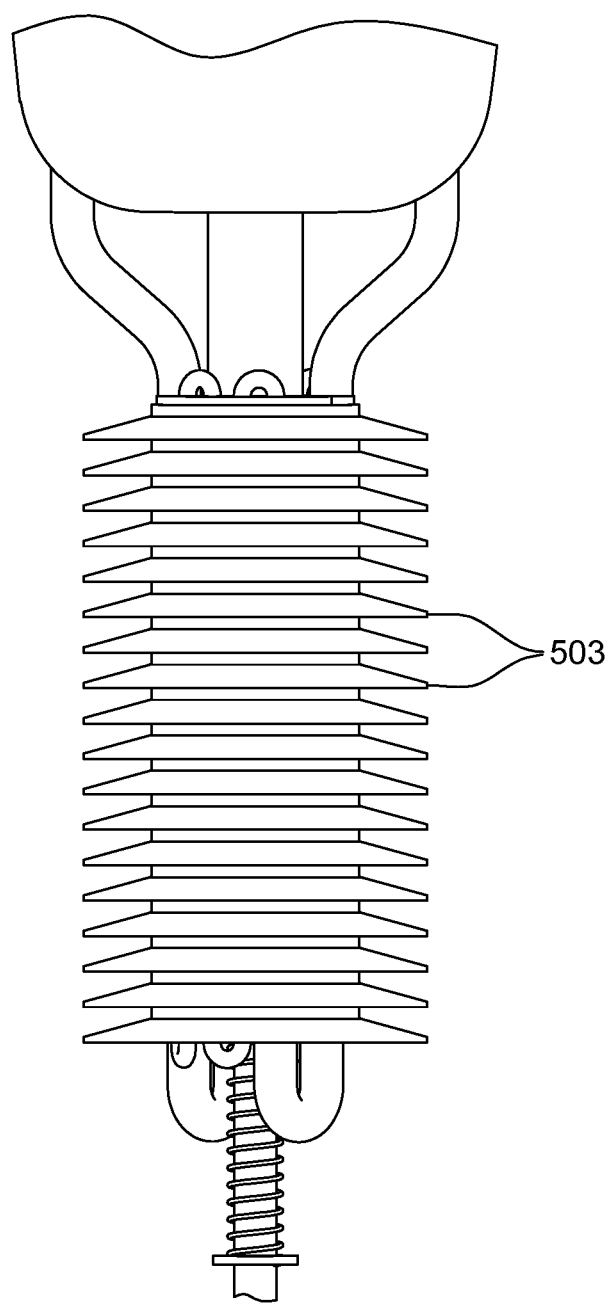
FIG. 6 is an alternate embodiment of an apparatus, in accordance with one or more aspects of the present invention.

In one or more embodiments, the plurality of thermally conductive fins can be formed integral with the thermally conductive structure 501, or can be attached, such as by soldering, welding, or braising onto an outer surface of the thermally conductive structure. Those skilled in the art will understand that more, or less, thermally conductive fins, and other attachment mechanisms, can be employed. Further, the orientation of the thermally conductive fins can be varied, depending on the application. For instance, FIG. 6 illustrates cooling device 110 of FIGS. 5A-5I, with a configuration and/or orientation of the plurality of thermally conductive fins 503 of the heat exchanger angled, for instance, to promote a natural convective cooling airflow across the fins, and thereby facilitate extraction of heat from coolant passing through the heat exchanger of the cooling device.

FIGS. 7A-7E depict an alternate embodiment of a cooling apparatus with a cooling device 110', such as cooling device 110 described above in connection with FIGS. 1-6.

Figure 7A:
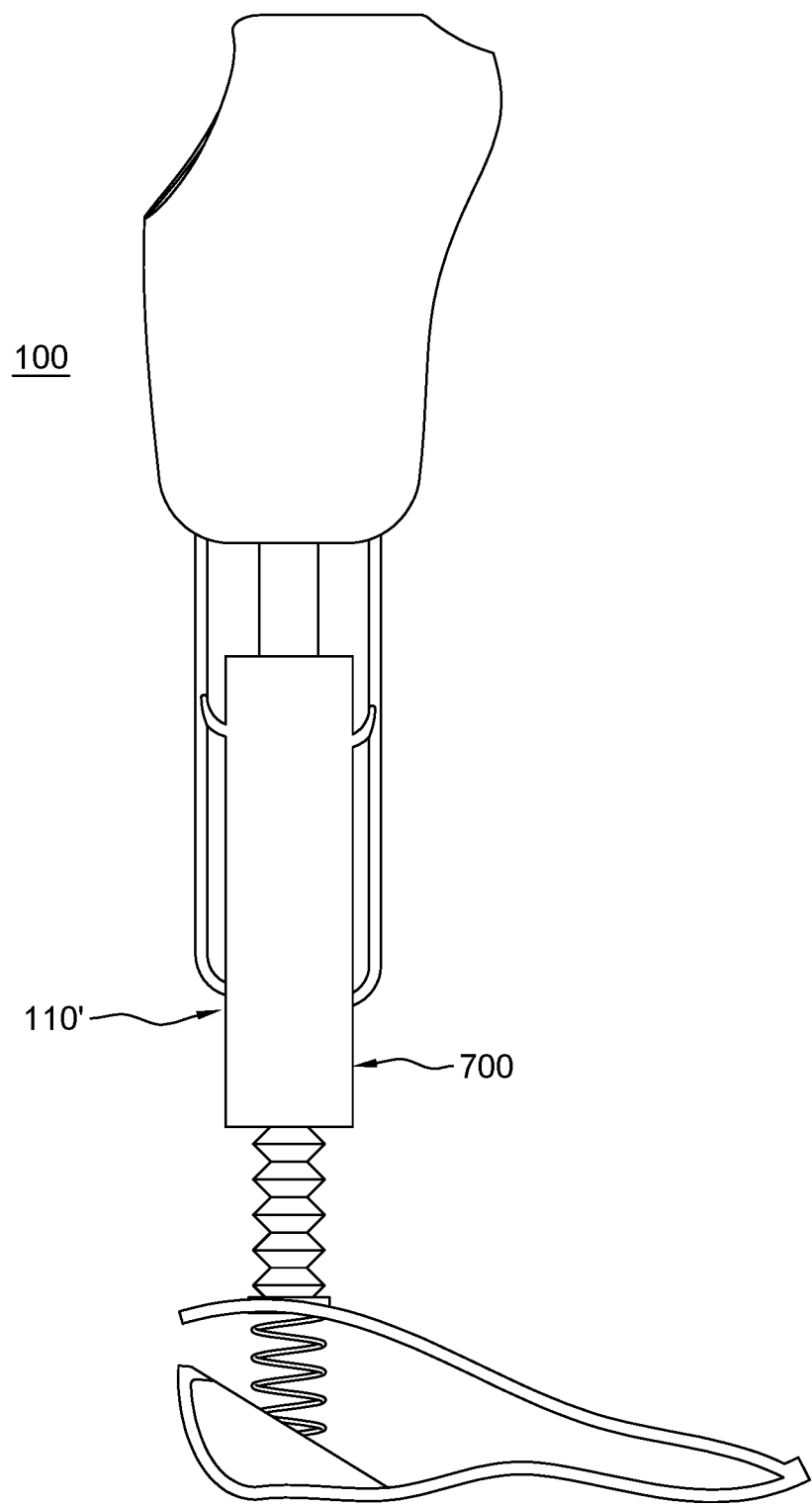
FIGS. 7A-7E depict another embodiment of an apparatus, in accordance with one or more aspects of the present invention.
Figure 7B:
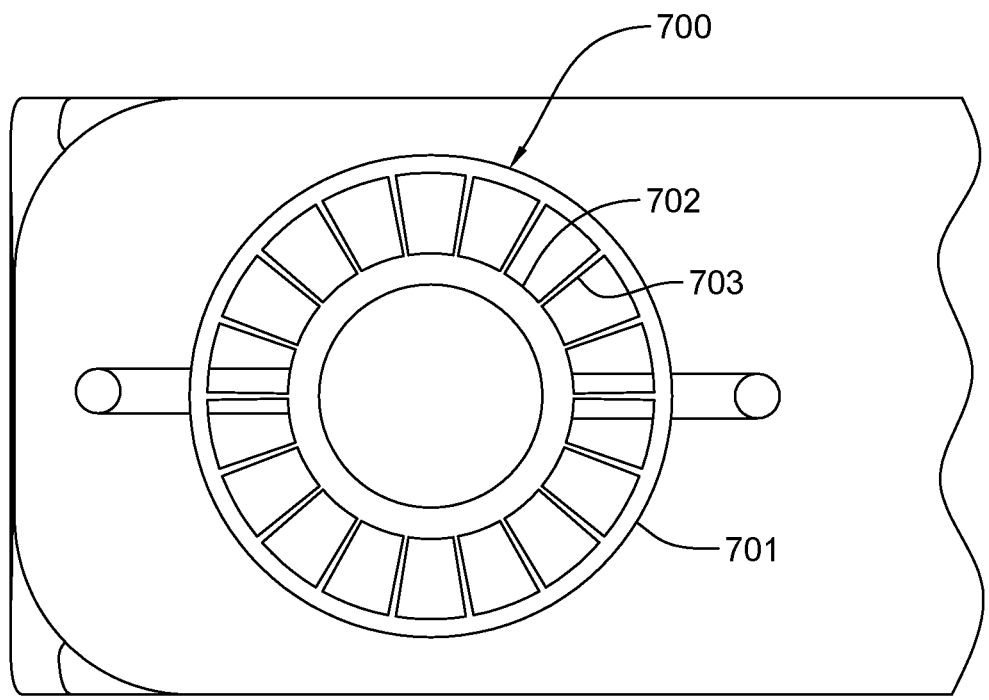

As illustrated in FIGS. 7A & 7B, the cooling device 110' is again illustrated as being integrated with a prosthesis 100 forming, for instance, a portion of the support structure in the example of the prosthetic leg. Coolant return and supply hoses or lines connect cooling device 110' and the portion of the coolant loop within the device to be cooled, such as the portion of the coolant loop within or near the prosthetic socket-to-individual limb interface (in one embodiment). Cooling device 110' includes a heat sink 700 which, in one embodiment, includes an outer thermally conductive structure 701, an inner thermally conductive structure 702, and a plurality of thermally conductive fins 703 oriented vertically between and coupling the thermally conductive outer and inner structures 701, 702. In one or more embodiments, thermally conductive outer structure 701 and thermally conductive inner structure 702 can be, for instance, respective cylindrical structures, with the thermally conductive fins being coupled to both structures and oriented vertically. In one or more embodiments, thermally conductive structure 702 includes one or more channels or tube sections in contact with, for instance, an inner surface of thermally conductive inner structure 702, such that heat passes from coolant within the channel(s) or tube section(s), through the inner thermally conductive structure 702, to the plurality of thermally conductive fins 703, for dissipation to ambient air about the cooling device. In the embodiment of FIGS. 7A-7E, the plurality of thermally conductive fins 703 are illustrated in a vertical orientation, by way of example only. Also, note that in one or more implementations, the inner and outer thermally conductive structures 701, 702, as well as the thermally conductive fins 703, can be formed of the same thermally conductive material(s) or different thermally conductive material(s), such as the same or different metal material(s). As liquid coolant flows through the channel(s) or tube section(s) within, or associated with, inner thermally conductive structure 702, the coolant cools by conduction of heat across inner thermally conductive structure 702 to thermally conductive fins 703 for dissipation to the ambient air.

Figure 7C:
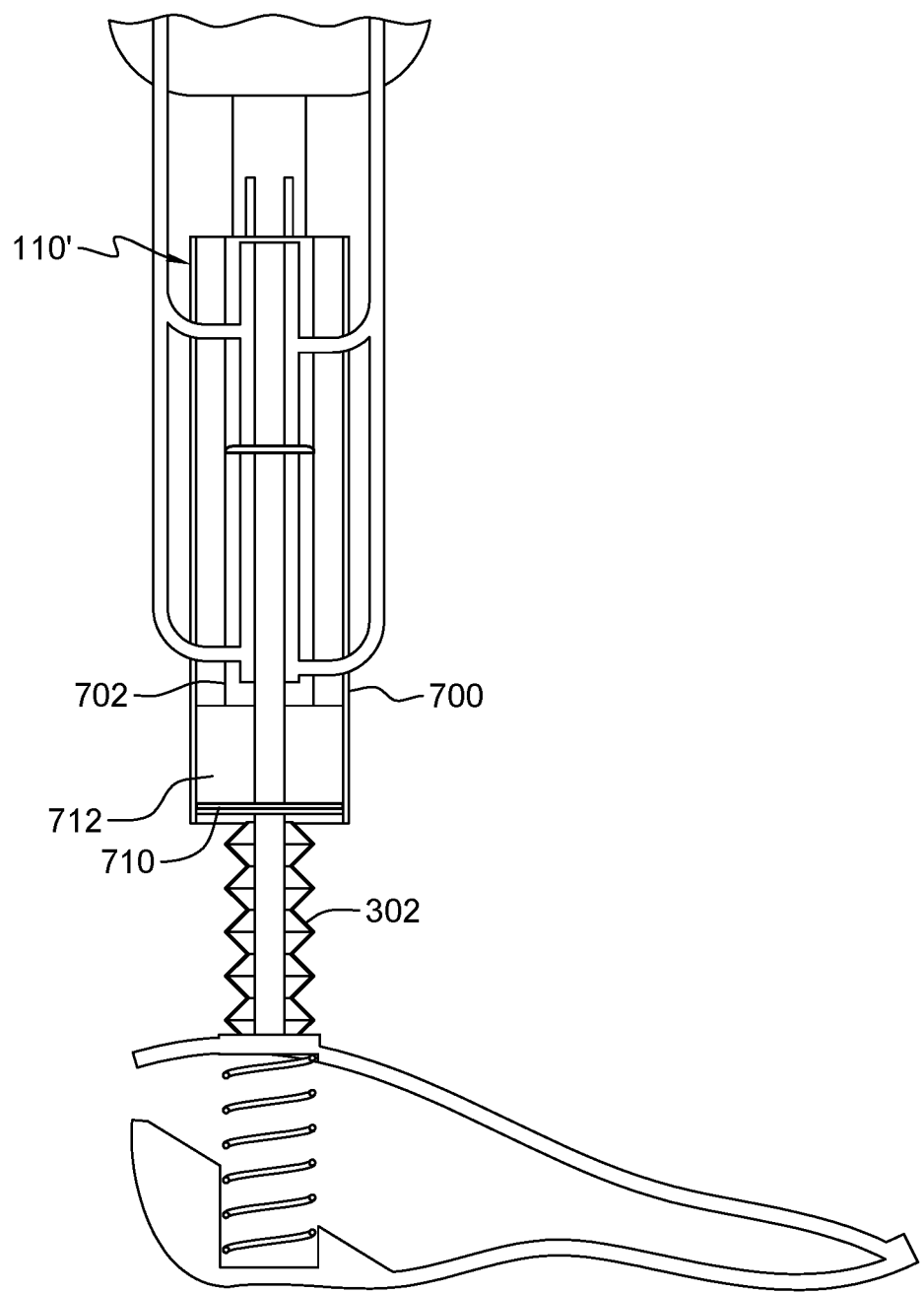
Figure 7D:
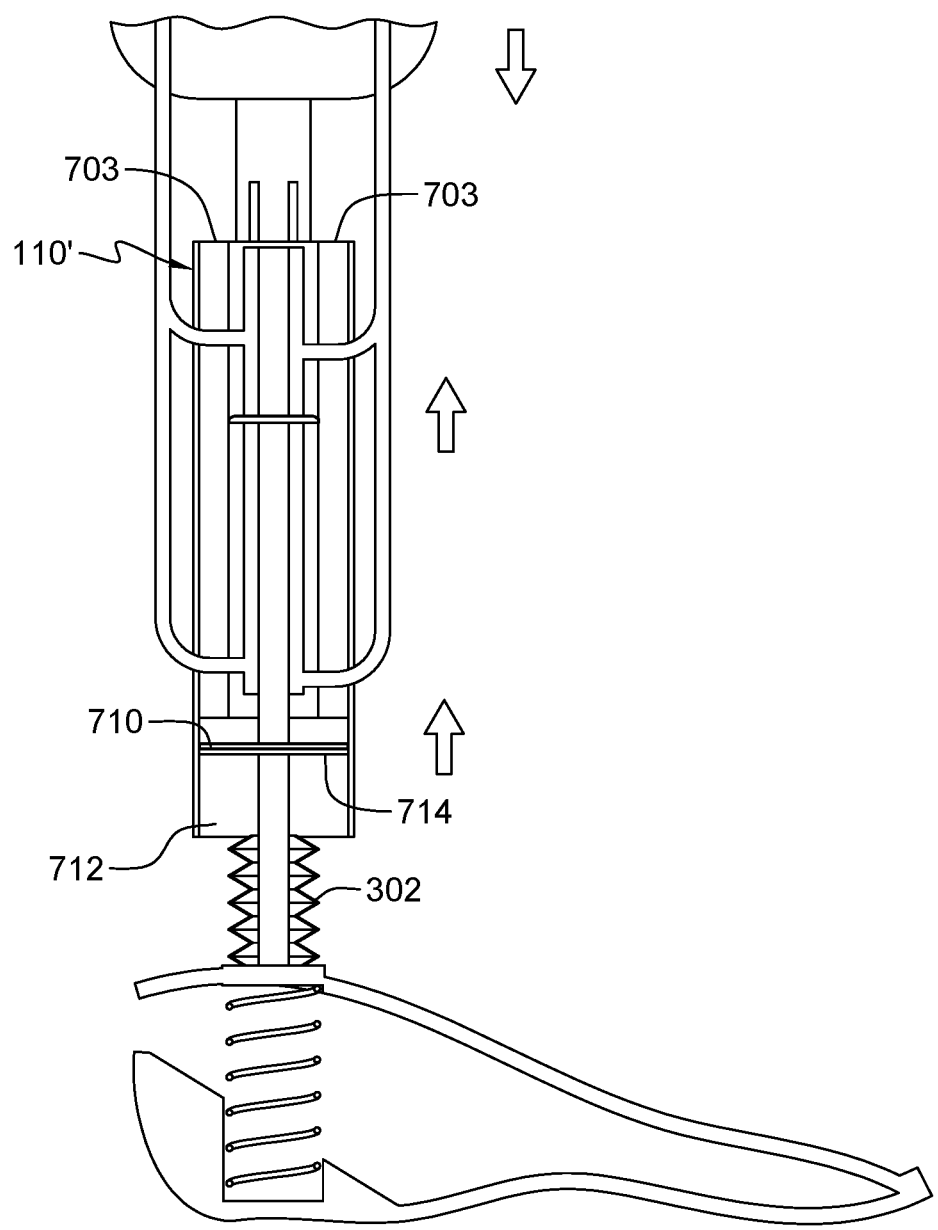
Figure 7E:
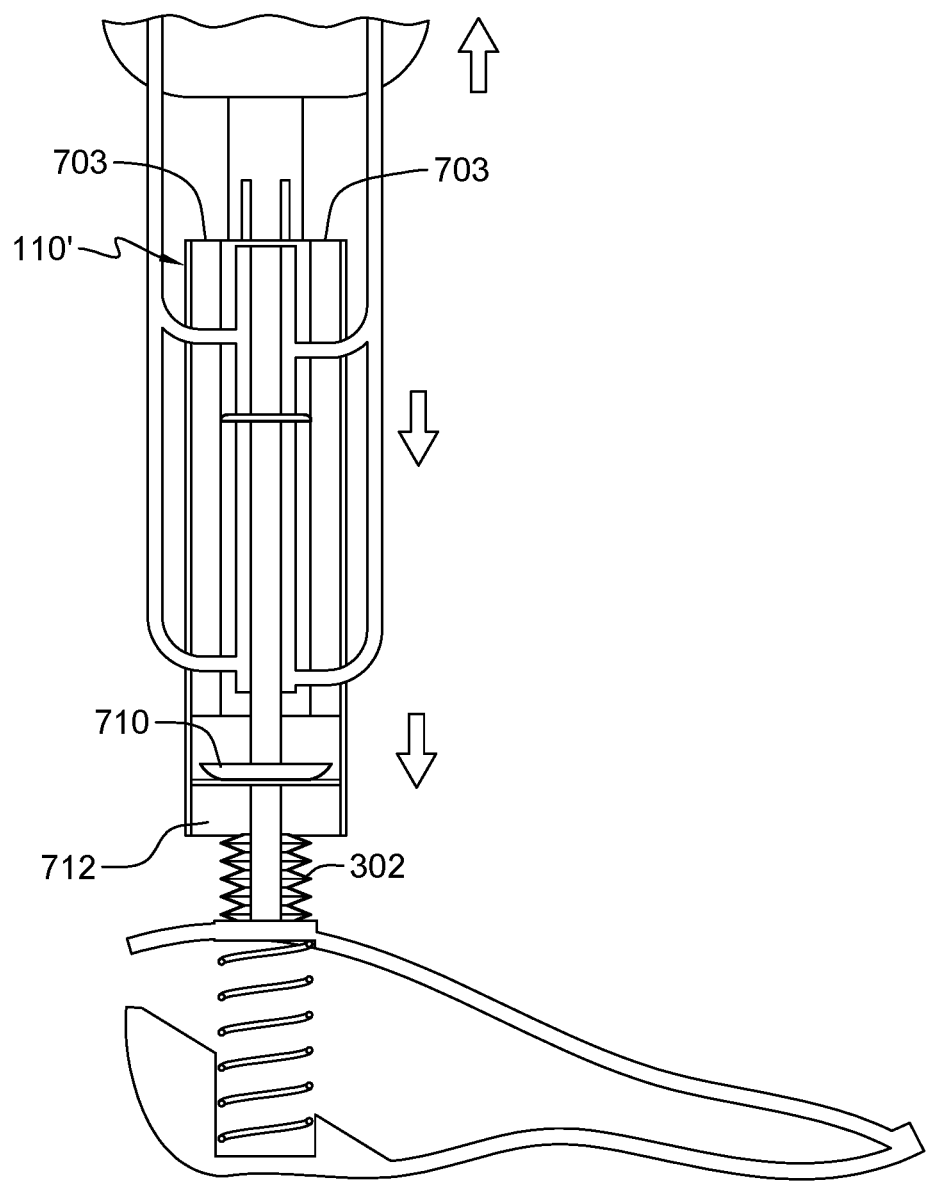

Convection of heat to the ambient air can be facilitated by provision of an air valve 710 within an air-chamber 712 of cooling device 110'. FIGS. 7C-7E illustrate one operational embodiment of such an air valve. In FIG. 7C, air valve 710 is shown flat within air chamber 712 of the cooling device embodiment, with the spring at a nominal, uncompressed state. In FIG. 7D, the individual steps on the prosthetic leg, with the individual's weight compressing spring 302, moving the pump piston up within the pump housing, and moving air valve 710 up within the air chamber 712, as illustrated. During this action, air valve 710 remains flat against a base frame 714 and moves upward in air chamber 712 to push air up across the vertically-oriented, plurality of thermally conductive fins 703 of cooling device 110'. Along with this action, spring 302 compresses. As illustrated in FIG. 7E, when the individual releases their weight from the prosthesis by, for instance, lifting up the prosthetic leg, spring 302 releases, moving the pump piston within the pump housing downward (in the example of FIG. 7E), as well as moving air valve 710 downward. In one implementation, air valve 710 is a flexible valve, and as the valve moves downwards within air chamber 712, the valve is selected or fabricated to curve upward towards its outer edge, allowing air to move around the valve into air chamber 712.

Figure 8A:
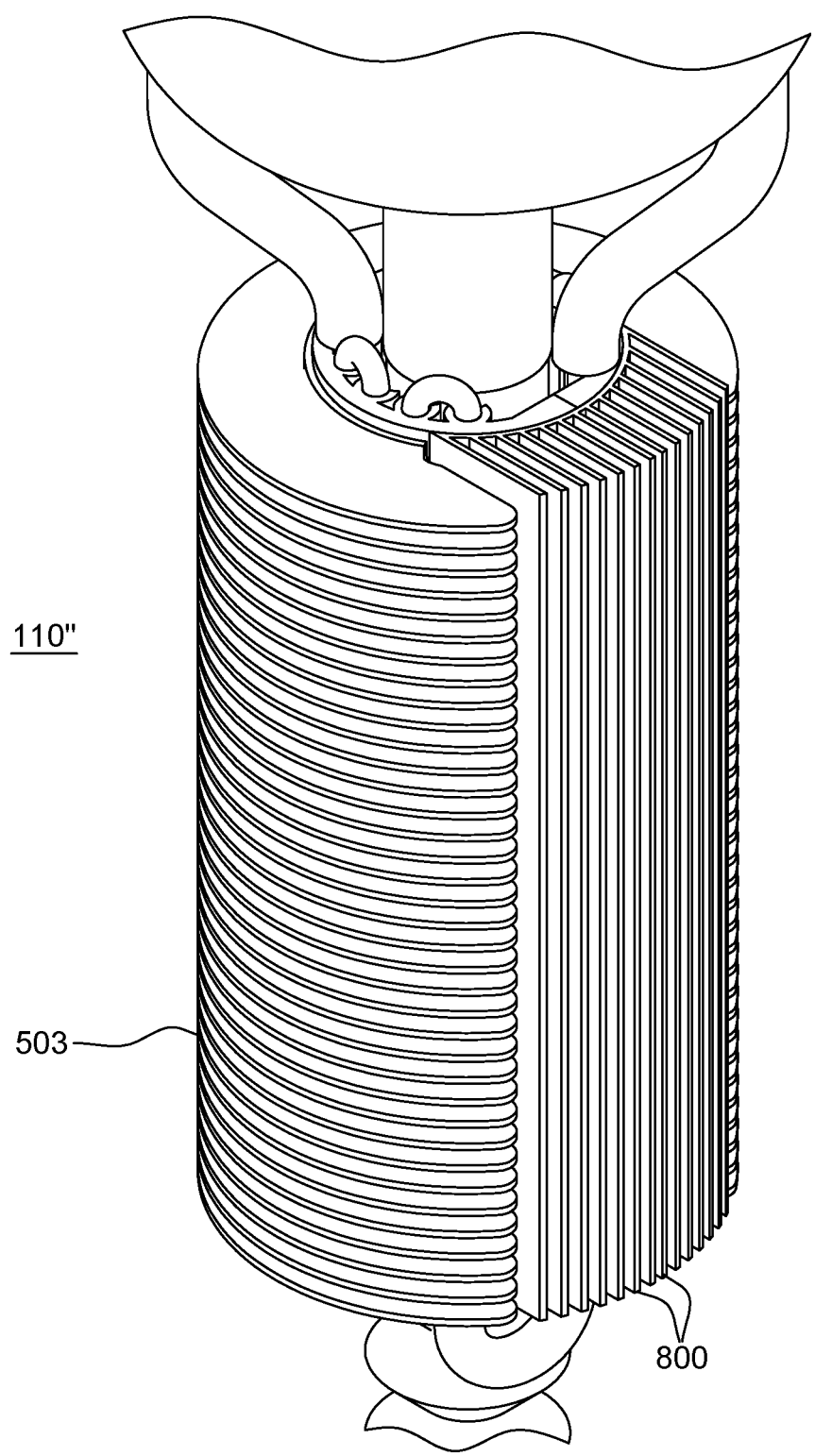
FIGS. 8A-8B depict a further embodiment of an apparatus, in accordance with one or more aspects of the present invention.
Figure 8B:
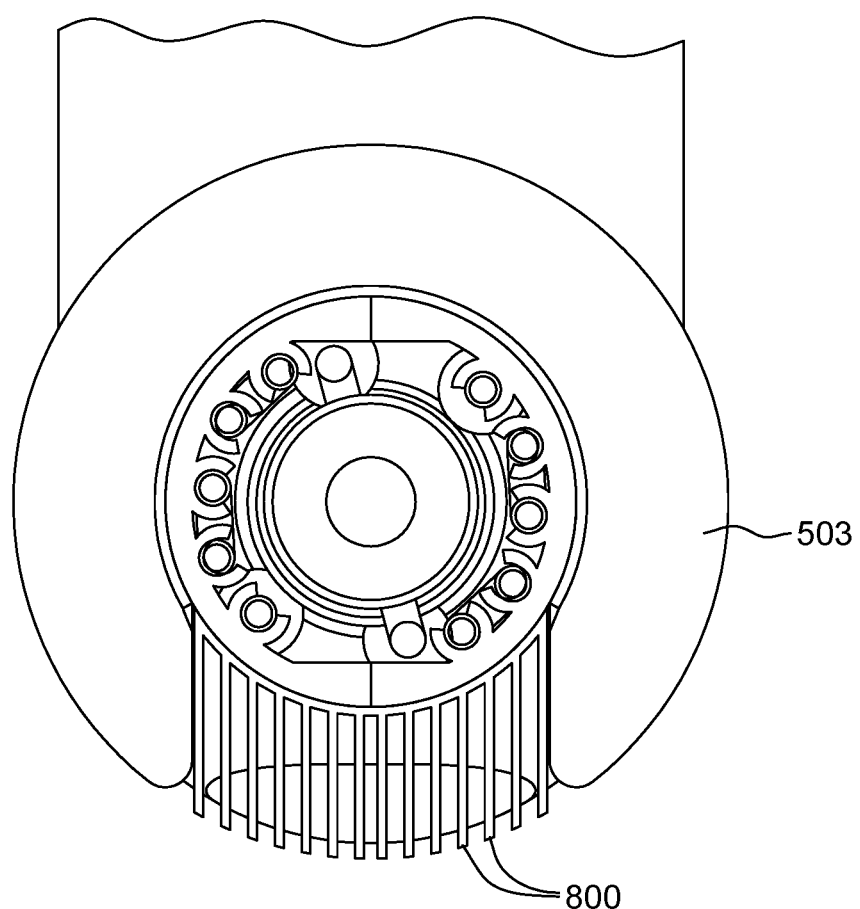

As noted, the orientation of the thermally conductive fins can vary, depending on the application. FIGS. 8A & 8B depict a further variation of a cooling device 110", integrated within a prosthesis such as described herein. In this embodiment, cooling device 110" is similar to cooling device 110 described above in connection with FIGS. 1-5I, with the exception being that the thermally conductive fins 503 are modified to include a portion of vertically-oriented, thermally conductive fins 800. This can be accomplished by, for instance, removing a selected portion of the thermally conductive fins 503 to allow for inclusion of vertically-oriented fins 800. Vertically-oriented fins 800 can facilitate cooling the coolant when the individual is, for instance, moving less, with the vertically-oriented thermally conductive fins 800 improving dissipation of heat from coolant within cooling device 110" in that situation, while still allowing the horizontal thermally conductive fins 503 to facilitate heat dissipation when the individual increases movement of the prosthesis. In general, multi-directional fins can be included in a cooling device such as disclosed herein to ensure efficient heat dissipation from the apparatus to ambient air during, for instance, a variety of prosthetic movements, including the case of an individual stepping down on a prosthetic leg while sitting.

Those skilled in the art will note from the description provided herein that a cooling apparatus is presented for, for instance, integration with a device worn by an individual to facilitate cooling the device at the interface between the device and the individual. In one embodiment, the apparatus includes a mechanical coolant pump to facilitate pumping a coolant through a coolant loop. The apparatus couples to an individual and the mechanical coolant pump is physically powered by a specified movement of the individual to pump coolant. The coolant pumped by the mechanical coolant pump is circulated by the coolant loop through the device to be cooled associated with the individual, such as a device worn by the individual. In one or more implementations, the cooling apparatus is integrated as part of a prosthesis, with the coolant pumped by the mechanical coolant pump being circulated by the coolant loop through a prosthetic socket of the prosthesis worn by the individual to cool the prosthetic socket. In one or more implementations, the cooling apparatus is integrated as part of the prosthesis, such as part of the support structure of the prosthesis. Where the prosthesis is a prosthetic leg, the specified movement can be a stepping action of the individual on the prosthetic leg.

In one or more implementations, the mechanical coolant pump includes a pump housing to couple in fluid communication to the coolant loop, and a pump piston slidable within the pump housing. The pump piston is physically powered with the specified movement of the individual to facilitate, at least in part, pumping the coolant through the coolant loop.

In one embodiment, the cooling apparatus further includes a spring, with the spring biasing the pump piston in a first direction within the pump housing. In one exemplary embodiment, the pump piston divides the pump housing into a first coolant chamber and a second coolant chamber. The first coolant chamber has a first coolant inlet and a first coolant outlet, and the second coolant chamber has a second coolant inlet and a second coolant outlet. With the first and second coolant inlets and the first and second coolant outlets coupled in fluid communication with the coolant loop, the specified movement of the individual moves the pump piston in a second direction within the pump housing, compressing the spring, and drawing the coolant into the first chamber through the first coolant inlet, concurrently pushing coolant from the second chamber through the second coolant outlet. Release from the specified movement of the individual allows the spring to move the pump piston in the first direction within the pump housing, drawing coolant into the second coolant chamber through the first coolant inlet, concurrently pushing coolant from the first coolant chamber through the first coolant outlet.

In one embodiment, the pump housing is an elongate pump housing, and the cooling apparatus further includes a heat sink. The heat sink includes at least one coolant tube section coupling in fluid communication at least one coolant chamber of the pump housing and the coolant loop, and a plurality of thermally conductive fins mechanically couple, at least in part, to the at least one coolant tube section to facilitate transfer of heat from coolant passing through the at least one coolant tube section to ambient air about the apparatus. In one or more embodiments, the cooling apparatus further includes an air valve which operates within an air chamber with the specified movement of the individual, and release of the specified movement of the individual, to force air across the plurality of thermally conductive fins, and which in one embodiment, include one or more vertically-oriented thermally conductive fins.

In one implementation, the plurality of thermally conductive fins include a first plurality of thermally conductive fins oriented in a first direction, and a second plurality of thermally conductive fins oriented in a second direction, where the first and second directions are different directions.

In one or more implementations, one or more adjustable valves can be provided within the cooling device, such as within a coolant tube section within the cooling device, to control a dampening level of the mechanical coolant pump in operation. In one or more implementations, the adjustable valves can be adjustable electronic valves with an appropriate control being provided as part of the cooling apparatus, but not to drive the mechanical coolant pump itself. In one or more implementations, a bypass valve can be coupled across the pump housing to allow a portion of coolant within the coolant loop to bypass the pump housing to facilitate control of coolant flow through the coolant loop via the mechanical coolant pump, and thereby control, for instance, the dampening effect of the mechanical coolant pump.

Figure 9:
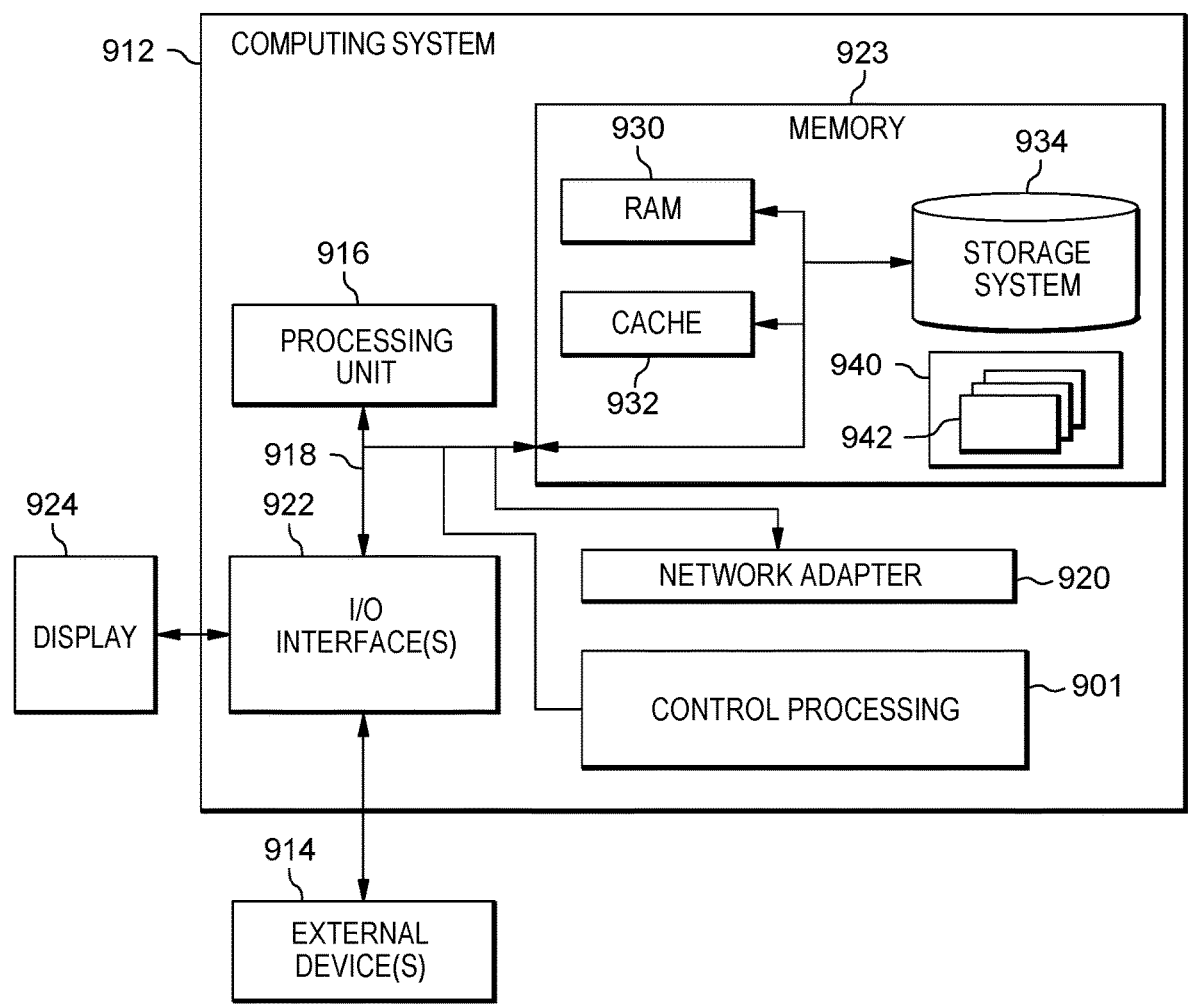
FIG. 9 depicts one embodiment of a computing system to implement, or facilitate implementing, control of one or more adjustable valves of a cooling device, in accordance with one or more aspects of the present invention.

By way of further example, FIG. 9 depicts one embodiment of a computing environment 900, which includes a computing system 912 configured to implement one or more aspects of the control disclosed herein. Examples of well-known computing systems, environments, and/or configurations that may be suitable for use with computer system 912 include, but are not limited to, a wireless computer, a handheld or laptop computer or device, a mobile phone, a programmable consumer electronic device, a tablet, a personal digital assistant (PDA), and the like.

Computing system 912 can be described in the general context of computer system-executable instructions, such as program modules, being executed by a computer system. Generally, program modules include routines, programs, objects, components, logic, data structures, and so on that perform particular tasks or implement particular abstract data types.

As depicted in FIG. 9, computing system 912, is shown in the form of a general-purpose computing device. The components of computing system 912 can include, but are not limited to, one or more processors or processing units 916, a system memory 923, and a bus 918 that couples various system components including system memory 923 to processor 916.

In one embodiment, processor 916 may be based on the z/Architecture® offered by International Business Machines Corporation, or other architectures offered by International Business Machines Corporation or other companies.

Bus 918 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing system 912 can include a variety of computer system readable media. Such media may be any available media that is accessible by computing system 912, and it includes both volatile and non-volatile media, removable and non-removable media.

System memory 923 can include computer system readable media in the form of volatile memory, such as random access memory (RAM) 930 and/or cache memory 932. Computing system 912 can further include other removable/non-removable, volatile/non-volatile computer system storage media. By way of example only, storage system 934 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media could be provided. In such instances, each can be connected to bus 918 by one or more data media interfaces. As described below, memory 923 can include at least one program product having a set (e.g., at least one) of program modules or code that are configured to carry out the functions of control embodiments of the invention.

Program/utility 940, having a set (at least one) of program modules 942, can be stored in memory 932 by way of example, and not limitation, as well as an operating system, one or more application programs, other program modules, and program data. Each of the operating system, one or more application programs, other program modules, and program data or some combination thereof, can include an implementation of a networking environment. Program modules 942 generally carry out the functions and/or methodologies of embodiments of the invention as described herein. Alternatively, a control processing facility, module, logic, etc., 901 can be provided within computing environment 912, as disclosed herein.

Computing system 912 can also communicate with one or more external devices 914 such as a keyboard, a pointing device, a display 924, etc.; one or more devices that enable a user to interact with computing system 912; and/or any devices (e.g., network card, modem, etc.) that enable computing system 912 to communicate with one or more other computing devices. Such communication can occur via Input/Output (I/O) interfaces 922. Still yet, computing system 912 can communicate with one or more networks such as a local area network (LAN), a general wide area network (WAN), and/or a public network (e.g., the Internet) via network adapter 920. As depicted, network adapter 920 communicates with the other components of computing system, 912, via bus 918. It should be understood that although not shown, other hardware and/or software components could be used in conjunction with computing system 912. Examples, include, but are not limited to: microcode, device drivers, redundant processing units, external disk drive arrays, RAID systems, tape drives, and data archival storage systems, etc.

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The control aspects of the present invention may be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more control aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more control embodiments.

As a further aspect, a computing infrastructure may be deployed comprising integrating computer readable code into a computing system, in which the control code in combination with the computing system is capable of performing one or more embodiments.

As yet a further aspect, a process for integrating control computing infrastructure comprising integrating computer readable code into a computer system can be provided. The computer system comprises a computer readable medium, in which the computer medium comprises one or more embodiments. The code in combination with the computer system is capable of performing one or more control embodiments.

Although various embodiments are described above, these are only examples. For example, computing environments of other architectures can be used to incorporate and use one or more control embodiments. Further, different instructions, instruction formats, instruction fields and/or instruction values may be used. Many variations are possible.

Further, other types of computing environments can benefit and be used. As an example, a data processing system suitable for storing and/or executing program code is usable that includes at least two processors coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. An apparatus comprising:
    a mechanical coolant pump to facilitate pumping a coolant through a coolant loop, the apparatus to couple to an individual and the mechanical coolant pump being physically-powered by a specified movement of the individual to pump coolant;
    wherein the coolant pumped by the mechanical coolant pump comprises a liquid coolant, and the liquid coolant is circulated by the coolant loop through a device associated with the individual to cool the device; and
    a heat sink to cool the liquid coolant within the coolant loop.

2. The apparatus of claim 1, wherein the mechanical coolant pump comprises:
    a pump housing to couple in fluid communication to the coolant loop; and
    a pump piston slidable within the pump housing, the pump piston being physically powered with the specified movement of the individual to facilitate, at least in part, pumping the coolant through the coolant loop.

3. The apparatus of claim 2, further comprising a spring, the spring biasing the pump piston in a first direction within the pump housing.

4. The apparatus of claim 3, wherein:
    the pump piston divides the pump housing into a first coolant chamber and a second coolant chamber;
    the first coolant chamber has a first coolant inlet and a first coolant outlet, and the second coolant chamber has a second coolant inlet and a second coolant outlet; and
    with the first and second coolant inlets and first and second coolant outlets coupled in fluid communication with the coolant loop, the specified movement of the individual is configured to move the pump piston in a second direction within the pump housing, compressing the spring, and drawing coolant into the first chamber through the first coolant inlet, concurrently pushing coolant from the second chamber through the second coolant outlet, and release from the specified movement of the individual allows the spring to move the pump piston in the first direction within the pump housing, drawing coolant into the second coolant chamber through the second coolant inlet, concurrently pushing coolant from the first coolant chamber through the first coolant outlet.

5. The apparatus of claim 2, wherein the pump housing is an elongate pump housing, and wherein the apparatus further comprises a heat sink, the heat sink comprising:
    at least one coolant tube section coupling in fluid communication at least one coolant chamber of the pump housing and the coolant loop; and
    a plurality of thermally conductive fins mechanically coupled, at least in part, to the at least one coolant tube section to facilitate transfer of heat from coolant passing through the at least one coolant tube section to ambient air about the apparatus.

6. The apparatus of claim 5, wherein the apparatus further comprises an air valve to operate within a chamber with the specified movement and release of the specified movement of the individual to force air across the plurality of thermally conductive fins.

7. The apparatus of claim 5, wherein the plurality of thermally conductive fins comprises a first plurality of thermally conductive fins oriented in a first direction, and a second plurality of thermally conductive fins oriented in a second direction, the first direction and the second direction being different directions.

8. The apparatus of claim 5, further comprising one or more adjustable valves within the at least one coolant tube section to control a dampening level of the mechanical coolant pump in operation.

9. The apparatus of claim 5, further comprising a bypass valve coupled across the pump housing to allow a portion of coolant within the coolant loop to bypass the pump housing to facilitate control of coolant flow through the coolant loop via the mechanical coolant pump.

10. An apparatus comprising:
a mechanical coolant pump to facilitate pumping a coolant through a coolant loop, the apparatus to couple to an individual and the mechanical coolant pump being physically-powered by a specified movement of the individual to pump coolant;
wherein the coolant pumped by the mechanical coolant pump comprises a liquid coolant, and the liquid coolant is circulated by the coolant loop through a device associated with the individual to cool the device; and
a heat sink to cool the liquid coolant within the coolant loop.

11. The apparatus of claim 10, wherein the prosthesis is a prosthetic leg, the specified movement is a stepping action of the individual on the prosthetic leg, and the mechanical coolant pump is integrated as part of the prosthetic leg.

12. The apparatus of claim 10, wherein the mechanical coolant pump comprises:
a pump housing to couple in fluid communication to the coolant loop; and
a pump piston slidable within the pump housing, the pump piston being physically powered with the specified movement of the individual to facilitate, at least in part, pumping the coolant through the coolant loop.

13. The apparatus of claim 12, further comprising a spring, the spring biasing the pump piston in a first direction within the pump housing.

14. The apparatus of claim 13, wherein:
the pump piston divides the pump housing into a first coolant chamber and a second coolant chamber;
the first coolant chamber has a first coolant inlet and a first coolant outlet, and the second coolant chamber has a second coolant inlet and a second coolant outlet; and
with the first and second coolant inlets and first and second coolant outlets coupled in fluid communication with the coolant loop, the specified movement of the individual is configured to move the pump piston in a second direction within the pump housing, compressing the spring, and drawing coolant into the first chamber through the first coolant inlet, concurrently pushing coolant from the second chamber through the second coolant outlet, and release from the specified movement of the individual allows the spring to move the pump piston in the first direction within the pump housing, drawing coolant into the second coolant chamber through the second coolant inlet, concurrently pushing coolant from the first coolant chamber through the first coolant outlet.

15. The apparatus of claim 12, wherein the pump housing is an elongate pump housing, and wherein the apparatus further comprises a heat sink, the heat sink comprising:
at least one coolant tube section coupling in fluid communication at least one coolant chamber of the pump housing and the coolant loop; and
a plurality of thermally conductive fins mechanically coupled, at least in part, to the at least one coolant tube section to facilitate transfer of heat from coolant passing through the at least one coolant tube section to ambient air about the apparatus.

16. The apparatus of claim 15, wherein the mechanical coolant pump further comprises an air valve to operate within an air chamber with the specified movement and release of the specified movement of the individual to force air across the plurality of thermally conductive fins.

17. The apparatus of claim 15, wherein the plurality of thermally conductive fins comprises a first plurality of thermally conductive fins oriented in a first direction, and a second plurality of thermally conductive fins oriented in a second direction, the first direction and the second direction being different directions.

18. A method comprising:
providing a mechanical coolant pump to facilitate pumping a coolant through a coolant loop, the mechanical coolant pump being physically powered to pump coolant with a specified movement of an individual;
the mechanical coolant pump being provided as part of a prosthesis to be worn by the individual, wherein in operation, the coolant pumped by the mechanical coolant pump comprises a liquid coolant and the liquid coolant is circulated by the coolant loop through a prosthetic socket of the prosthesis when worn by the individual to cool the prosthetic socket; and
a heat sink to cool the liquid coolant within the coolant loop.

19. The method of claim 18, wherein the prosthesis is a prosthetic leg, the specified movement is a stepping action of the individual on the prosthetic leg, and the mechanical coolant pump is integrated as part of the prosthetic leg.

20. The method of claim 18, wherein the mechanical coolant pump comprises:
a pump housing to couple in fluid communication to the coolant loop;
a pump piston slidable within the pump housing, the pump piston being physically powered with the specified movement of the individual to facilitate, at least in part, pumping the coolant through the coolant loop;
a spring biasing the pump piston in a first direction within the pump housing; and
wherein:
the pump piston divides the pump housing into a first coolant chamber and a second coolant chamber;
the first coolant chamber has a first coolant inlet and a first coolant outlet, and the second coolant chamber has a second coolant inlet and a second coolant outlet; and
with the first and second coolant inlets and first and second coolant outlets coupled in fluid communication with the coolant loop, the specified movement of the individual is configured to move the pump piston in a second direction within the pump housing, compressing the spring, and drawing coolant into the first chamber through the first coolant inlet, concurrently pushing coolant from the second chamber through the second coolant outlet, and release from the specified movement of the individual allows the spring to move the pump piston in the first direction within the pump housing, drawing coolant into the second coolant chamber through the second coolant inlet, concurrently pushing coolant from the first coolant chamber through the first coolant outlet.

* * * * *